US011607125B2

(12) United States Patent
Morgan et al.

(10) Patent No.: US 11,607,125 B2
(45) Date of Patent: Mar. 21, 2023

(54) METHODS AND SYSTEMS FOR ASSESSING PHOTORECEPTOR FUNCTION

(71) Applicant: The Trustees of the University of Pennsylvania, Philadelphia, PA (US)

(72) Inventors: Jessica I. W. Morgan, Mullica Hill, NJ (US); David H. Brainard, Merion Station, PA (US); Robert F. Cooper, Philadelphia, PA (US); William S. Tuten, Narberth, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 941 days.

(21) Appl. No.: 16/389,942

(22) Filed: Apr. 20, 2019

(65) Prior Publication Data

US 2019/0320892 A1   Oct. 24, 2019

Related U.S. Application Data

(60) Provisional application No. 62/660,868, filed on Apr. 20, 2018.

(51) Int. Cl.
*A61B 3/12* (2006.01)
*A61B 3/00* (2006.01)
*A61B 3/14* (2006.01)

(52) U.S. Cl.
CPC .............. *A61B 3/12* (2013.01); *A61B 3/0025* (2013.01); *A61B 3/14* (2013.01)

(58) Field of Classification Search
CPC ............ A61B 3/12; A61B 3/0025; A61B 3/14

USPC .......................................................... 600/476
See application file for complete search history.

(56) References Cited

U.S. PATENT DOCUMENTS

| 2005/0025810 | A1* | 2/2005 | Peyman ................... A61P 19/02 514/183 |
| 2009/0244484 | A1* | 10/2009 | Sharifzadeh ......... A61B 5/0059 351/221 |
| 2017/0325676 | A1* | 11/2017 | Lichtenauer ........... A61B 3/024 |
| 2018/0153399 | A1* | 6/2018 | Fink ......................... A61B 3/12 |
| 2021/0393122 | A1* | 12/2021 | Milea ....................... A61B 3/12 |

OTHER PUBLICATIONS

Ahnelt, et al., "Identification of a subtype of cone photoreceptor, likely to be blue sensitive, in the human retina," J Comp Neurol. Jan. 1, 1987;255(1):18-34.
Arshavsky, et al., "G proteins and phototransduction," Annu Rev Physiol. 2002;64:153-87.

(Continued)

*Primary Examiner* — Mohammed A Hasan
(74) *Attorney, Agent, or Firm* — Howson & Howson LLP; Colleen M. Schaller

(57) ABSTRACT

A method for non-invasive assessment of photoreceptor function in a mammalian subject comprises exposing a subject's eye to a visible light stimulus to initiate an intrinsic reflectance response in one or a population of photoreceptors and capturing multiple images of photoreceptor's intrinsic reflectance response to the stimulus. Patterns of variability in the intrinsic reflectance response of a single photoreceptor or population of photoreceptors are useful in diagnosis and treatment monitoring of an ocular condition, disease, disorder or a response to treatment for said ocular condition, disease or disorder.

23 Claims, 17 Drawing Sheets

(56) References Cited

OTHER PUBLICATIONS

Bedgood and Methda, "De-warping of images and improved eye tracking for the scanning laser ophthalmoscope," PLoS One. Apr. 3, 2017;12(4):e0174617.
Carroll, et al, "Estimates of L:M cone ratio from ERG flicker photometry and genetics," J Vis. 2002;2(8):531-42.
Chen, et al, "Multi-modal automatic montaging of adaptive optics retinal images," Biomed Opt Express. Nov. 3, 2016;7(12):4899-4918.
Cideciyan, et al, "Human cone visual pigment deletions spare sufficient photoreceptors to warrant gene therapy," Hum Gene Ther. Dec. 2013;24(12):993-1006. Epub Oct. 30, 2013.
Cooper et al, "Non-invasive assessment of human cone photoreceptor function," Biomed Opt Express. Oct. 19, 2017;8(11):5098-5112.
Cooper, et al, "Spatial and temporal variation of rod," Biomed Opt Express. Sep. 1, 2011;2(9):2577-89. Epub Aug. 11, 2011.
Dalkara and Sahel, "Gene therapy for inherited retinal degenerations," C R Biol. Mar. 2014;337(3):185-92. Epub Mar. 11, 2014.
Drexler W., "Ultrahigh-resolution optical coherence tomography," J Biomed Opt. Jan.-Feb. 2004;9(1):47-74.
Dubra and Harvey, "Registration of 2D images from fast scanning ophthalmic instruments," in Biomedical Image Registration, B. Fischer, B. Dawant, and C. Lorenz, eds. (Springer-Verlag, 2010), pp. 60-71.
Dubra and Sulai, "Reflective afocal broadband adaptive optics scanning ophthalmoscope," Biomed Opt Express. Jun. 1, 2011; 2(6): 1757-1768.
Duncan, et al, "High-resolution imaging with adaptive optics in patients with inherited retinal degeneration," Invest Ophthalmol Vis Sci. Jul. 2007;48(7):3283-91.
Garrioch, et al, "Repeatability of in vivo parafoveal cone density and spacing measurements," Optom Vis Sci. May 2012;89(5):632-43.
Giacalone, et al, "Concise review: patient-specific stem cells to interrogate inherited eye disease," Stem Cells Transl Med. Feb. 2016; 5(2): 132-140.
Grieve and Roorda, "Intrinsic signals from human cone photoreceptors," Invest Ophthalmol Vis Sci. Feb. 2008;49(2):713-9.
Hillmann, et al, "In vivo optical imaging of physiological responses to photostimulation in human photoreceptors," Proc Natl Acad Sci U S A. Nov. 15, 2016;113(46):13138-13143. Epub Oct. 11, 2016.
Hofer, et al, "Organization of the human trichromatic cone mosaic," J Neurosci. Oct. 19, 2005;25(42):9669-79.
Hofmann, et al, "Light-induced axial and radial shrinkage effects and changes of the refractive index in isolated bovine rod outer segments and disc vesicles: physical analysis of near infrared scattering changes," Biophys Struct Mech. 1981;8(1-2):67-93.
Hofmann, et al, "Measurements on fast light-induced light-scattering and -absorption changes in outer segments of vertebrate light sensitive rod cells," Biophys Struct Mech. Apr. 15, 1976;2(1):61-77.
Jonnal, et al, "Imaging outer segment renewal in living human cone photoreceptors," Opt Express. Mar. 1, 2010;18(5):5257-70.
Jonnal, et al, "In vivo functional imaging of human cone photoreceptors," Opt Express. Nov. 26, 2007;15(24):16141-60.
Kuhn, et al, "Interactions between photoexcited rhodopsin and GTP binding protein: kinetic and stoichiometric analyses from light-scattering changes," Proc Natl Acad Sci U S A. Nov. 1981; 78(11): 6873-6877.

Liang, et al, "Supernormal vision and high-resolution retinal imaging through adaptive optics," J Opt Soc Am A Opt Image Sci Vis. Nov. 1997;14(11):2884-92.
Maguire, et al., "Age-dependent effects of RPE65 gene therapy for Leber's congenital amaurosis: A phase 1 dose-escalation trial," Lancet. Nov. 7, 2009;374(9701):1597-605. Epub Oct. 23, 2009.
Makous, et al, "Retinal microscotomas revealed with adaptive-optics microflashes," Invest Ophthalmol Vis Sci. Sep. 2006;47(9):4160-7.
Morgan, et al, "High resolution adaptive optics retinal imaging of cellular structure in Choroideremia," Invest Ophthalmol Vis Sci. Oct. 2014; 55(10): 6381-6397.
Morgan, et al, "Light-induced retinal changes observed with high-resolution autofluorescence imaging of the retinal pigment epithelium," Invest. Ophthalmology & Visual Science. Aug. 2008;49(8):3715-3729.
Pallikaris, et al, "The reflectance of single cones in the living human eye," Invest Ophthalmol Vis Sci. Oct. 2003;44(10):4580-92.
Pircher, et al, "Temporal changes of human cone photoreceptors observed in vivo with SLO/OCT," Biomed Opt Express. Jan. 1, 2011; 2(1): 100-112.
Poloschek and Sutter, "The fine structure of multifocal ERG topographies," J. Vis. 2(8), 577-587 (2002).
Ratnam, et al., "Relationship between foveal cone structure and clinical measures of visual function in patients with inherited retinal degenerations," Invest Ophthalmol Vis Sci. Aug. 28, 2013;54(8):5836-47.
Rha, et al, "Variable optical activation of human cone photoreceptors visualized using a short coherence light source," Opt Lett. Dec. 15, 2009; 34(24): 3782-3784.
Roorda and Williams, "The arrangement of the three cone classes in the living human eye," Nature. Feb. 11, 1999;397(6719):520-2.
Roorda, et al, "Adaptive optics scanning laser ophthalmoscopy," Opt. Express 10(9), 405-412 (2002).
Schnapf, et al, "Visual transduction in cones of the monkey *Macaca fascicularis*," J. Physiol. 427:681-713 (Aug. 1990).
Sharpe, et al., "A luminous efficiency function, V*(λ), for daylight adaptation," J Vis. Dec. 21, 2005;5(11):948-68.
Talcott, et al, "Longitudinal study of cone photoreceptors during retinal degeneration and in response to ciliary neurotrophic factor treatment," Invest Ophthalmol Vis Sci. Apr. 6, 2011;52(5):2219-26.
Tam, et al, "Noninvasive visualization and analysis of parafoveal capillaries in humans," Invest Ophthalmol Vis Sci. Mar. 2010; 51(3): 1691-1698.
Van De Kraats, et al, "The pathways of light measured in fundus reflectometry," Vision Res. Aug. 1996; 36(15), 2229-2247.
Yizhar, et al, "Optogenetics in neural systems," Neuron. Jul. 14, 2011;71(1):9-34.
Zayit-Soudry, et al, "Cone structure imaged with adaptive optics scanning laser ophthalmoscopy in eyes with nonneovascular age-related macular degeneration," Invest Ophthalmol Vis Sci. Nov. 15, 2013;54(12):7498-509.
Zhang, et al, "Ciliary neurotrophic factor delivered by encapsulated cell intraocular implants for treatment of geographic atrophy in age-related macular degeneration," Proc Natl Acad Sci U S A. Apr. 12, 2011; 108(15): 6241-6245.
Ziiang, et al., "In vivo optophysiology reveals that G-protein activation triggers osmotic swelling and increased light scattering of rod photoreceptors," Proc Natl Acad Sci U S A. Apr. 4, 2017; 114(14): E2937-E2946. Published online Mar. 20, 2017.
Zhao and Yao "Intrinsic optical imaging of stimulus-modulated physiological responses in amphibian retina," Opt. Lett. 2008;33(4):342-344.

* cited by examiner

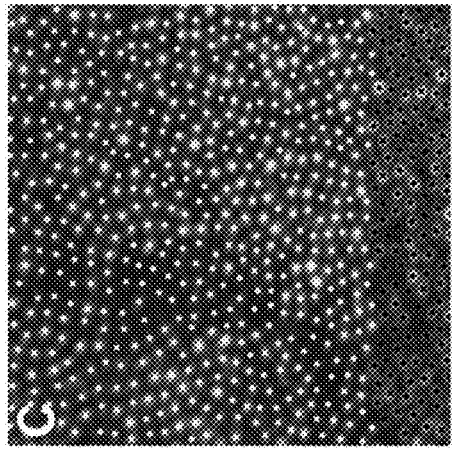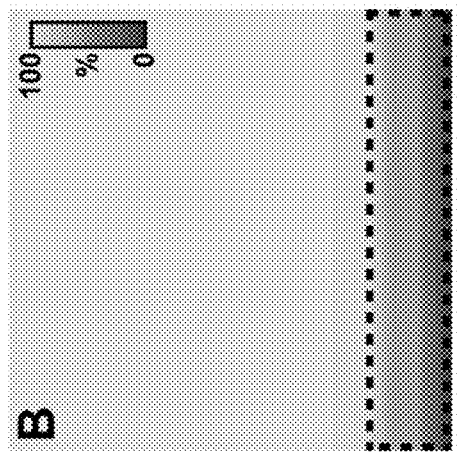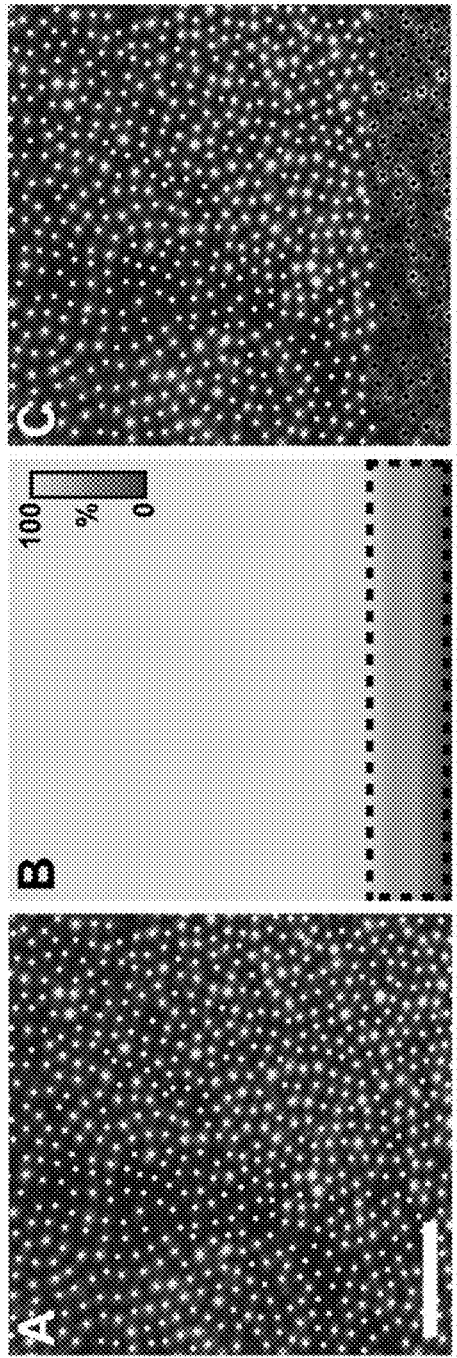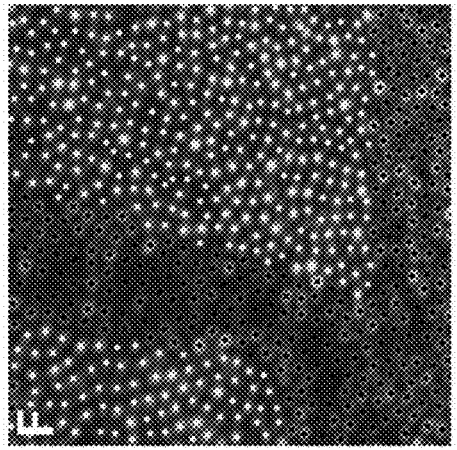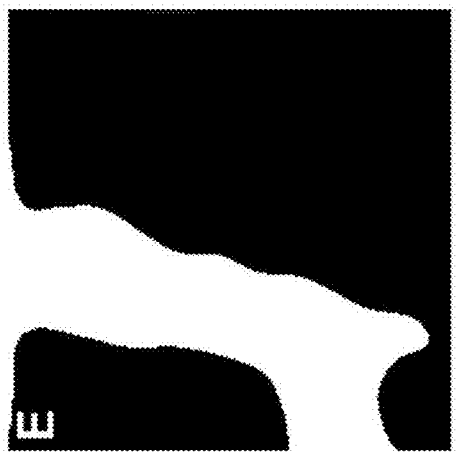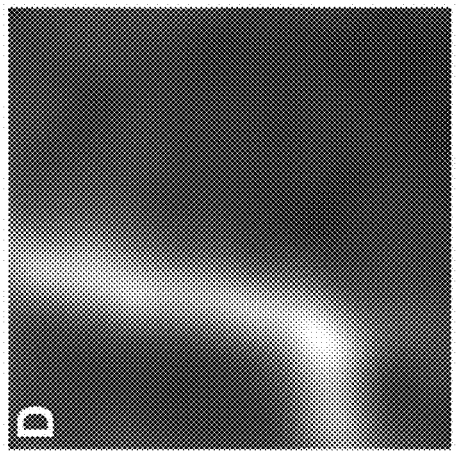
FIG. 1A FIG. 1B FIG. 1C
FIG. 1D FIG. 1E FIG. 1F

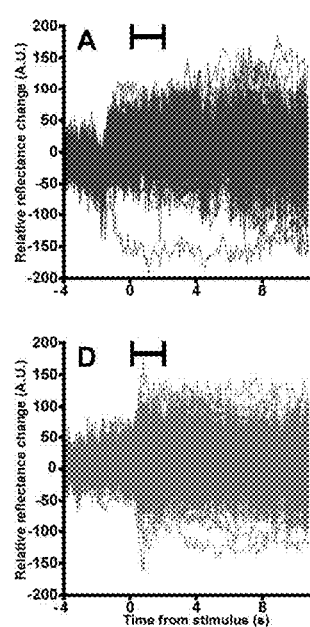
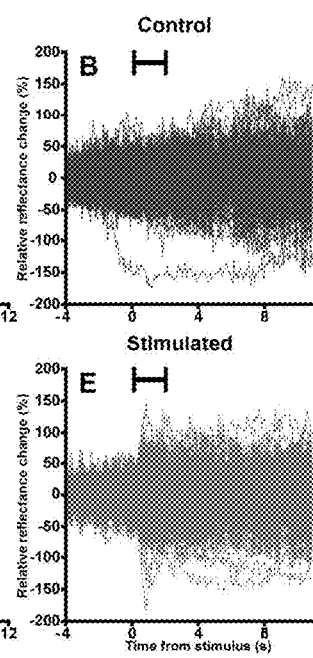
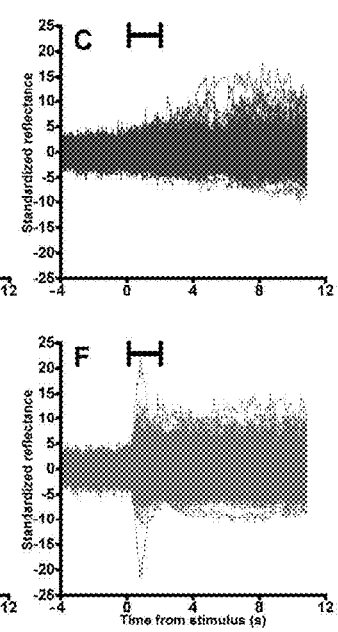
FIG. 2A    FIG. 2B    FIG. 2C
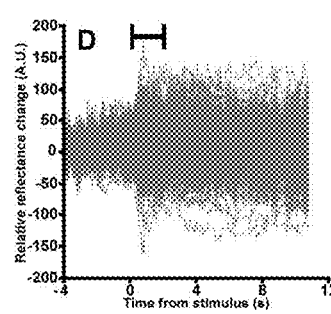
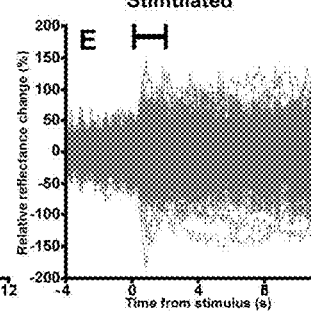
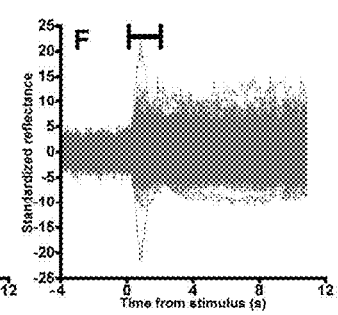
FIG. 2D    FIG. 2E    FIG. 2F

FIG. 10

Table 1. Reflectance response amplitudes averaged over all trials of a stimulus condition for each subject.

| | Sex | Age | 480 nm Irradiance (nW/deg²) | 480 nm Amplitude | 510 nm Irradiance (nW/deg²) | 510 nm Amplitude | 550 nm Irradiance (nW/deg²) | 550 nm Amplitude | 590 nm Irradiance (nW/deg²) | 590 nm Amplitude | 675 nm Irradiance (nW/deg²) | 675 nm Amplitude |
|---|---|---|---|---|---|---|---|---|---|---|---|---|
| 11002 | F | 36 | 6 | 0.07 | 2.4 | 0.03 | 2.2 | 0.02 | 2 | 0.03 | 37 | 0.02 |
| | | | 40 | 0.17 | 17 | 0.54 | 17 | 0.93 | 16 | 0.26 | 266 | 0.40 |
| | | | 145 | 0.40 | 140 | 1.41 | 138 | 1.41 | 147 | 0.73 | 2,260 | 0.85 |
| | | | | | 390 | 1.65 | 390 | 1.91 | 398 | 0.67 | 18,900 | 0.97 |
| 11015 | F | 26 | 6 | 0.04 | 1.9 | 0.06 | 1.4 | 0.06 | 2.1 | 0.04 | 37 | 0.05 |
| | | | 40 | 0.24 | 17 | 0.13 | 14 | 0.28 | 14 | 0.26 | 266 | 0.33 |
| | | | 145 | 0.16 | 124 | 0.63 | 138 | 0.94 | 141 | 0.90 | 2,260 | 0.81 |
| | | | | | 370 | 0.98 | 337 | 1.23 | 384 | 1.31 | 18,900 | 0.92 |
| 11043 | M | 34 | 6 | 0.03 | 2.1 | 0.12 | 2.5 | 0.02 | 2.1 | 0.06 | 37 | 0.00 |
| | | | 40 | 0.06 | 15 | 0.67 | 18 | 0.64 | 16 | 0.34 | 266 | 0.20 |
| | | | 145 | 0.15 | 148 | 2.00 | 140 | 2.42 | 140 | 1.67 | 2,260 | 1.08 |
| | | | | | 409 | 2.27 | 389 | 2.23 | 395 | 1.84 | 18,900 | 1.63 |
| 11046 | M | 57 | 4 | 0.05 | 2.5 | 0.04 | 1.5 | 0.01 | 4 | 0.02 | 37 | 0.09 |
| | | | 42 | 0.18 | 17 | 0.15 | 16 | 0.43 | 13 | 0.43 | 266 | 0.47 |
| | | | 150 | 0.72 | 150 | 0.81 | 150 | 1.56 | 142 | 1.45 | 2,260 | 1.08 |
| | | | | | 340 | 1.56 | 420 | 1.86 | 398 | 1.60 | 18,900 | 1.42 |
| 11049 | M | 30 | 5 | 0.08 | 2.1 | 0.05 | 2.2 | 0.00 | 2 | 0.06 | 37 | 0.00 |
| | | | 40 | 0.10 | 15 | 0.48 | 22 | 0.39 | 15 | 0.08 | 266 | 0.30 |
| | | | 147 | 0.19 | 148 | 1.51 | 130 | 1.35 | 142 | 1.50 | 2,260 | 0.99 |
| | | | | | 409 | 1.55 | 382 | 1.79 | 404 | 1.74 | 18,900 | 1.24 |
| Average | | 36.6 | 5.4 | 0.04 | 2.2 | 0.06 | 1.96 | 0.03 | 2.44 | 0.07 | 37 | 0.02 |
| | | | 40 | 0.11 | 16.2 | 0.36 | 17.4 | 0.56 | 14.8 | 0.35 | 266 | 0.36 |
| | | | 146.4 | 0.35 | 142 | 1.26 | 139.2 | 1.57 | 142.4 | 1.25 | 2,260 | 0.95 |
| | | | | | 383.6 | 1.64 | 383.6 | 1.78 | 395.8 | 1.42 | 18,900 | 1.14 |

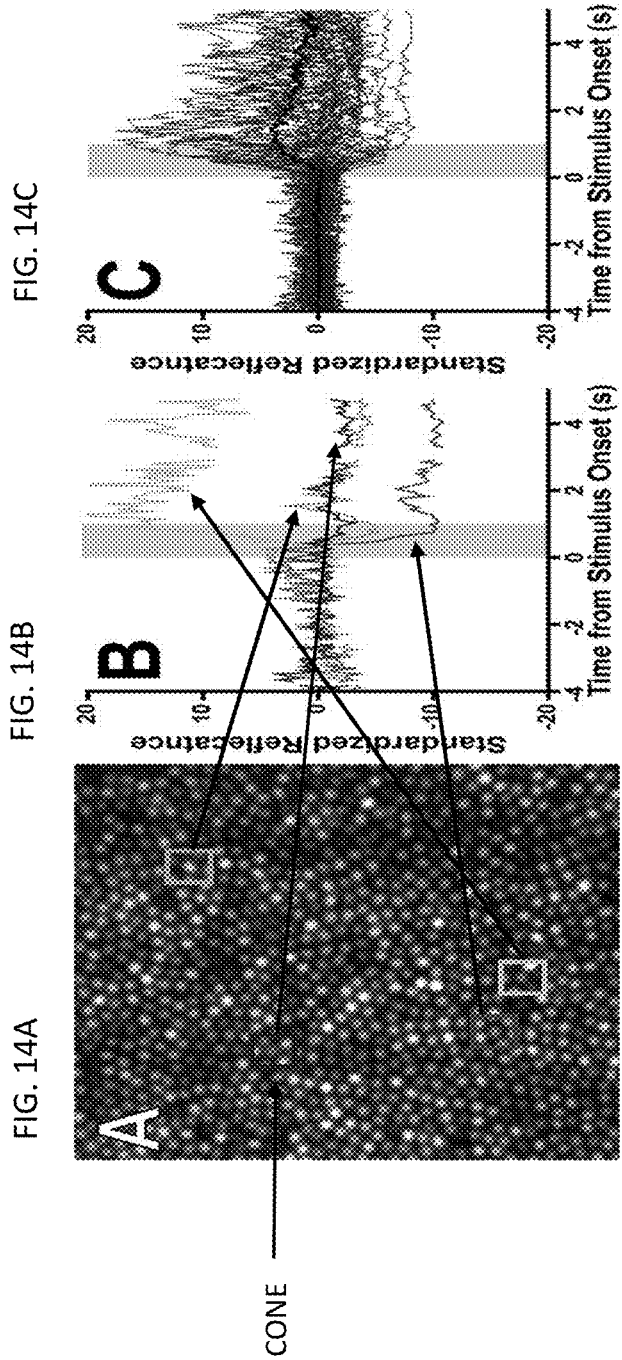

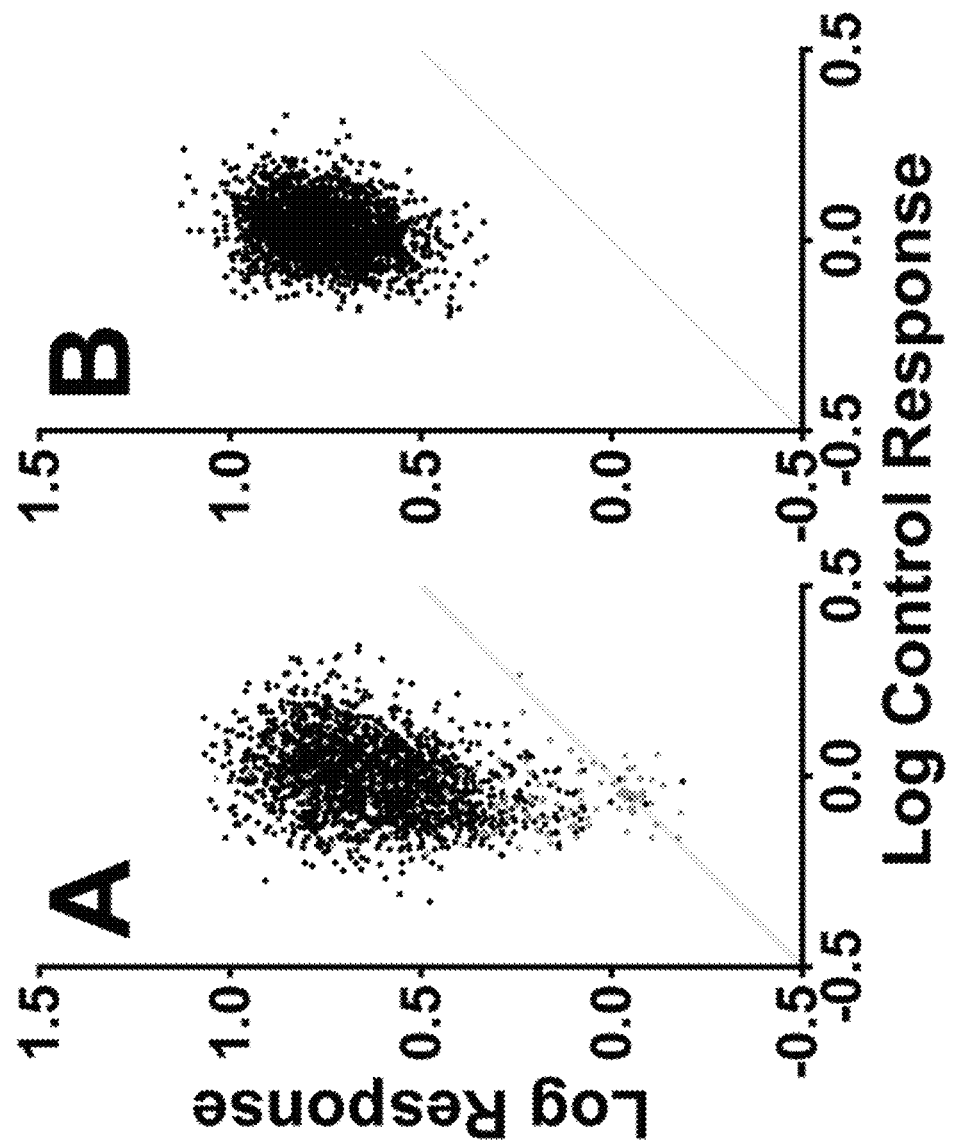

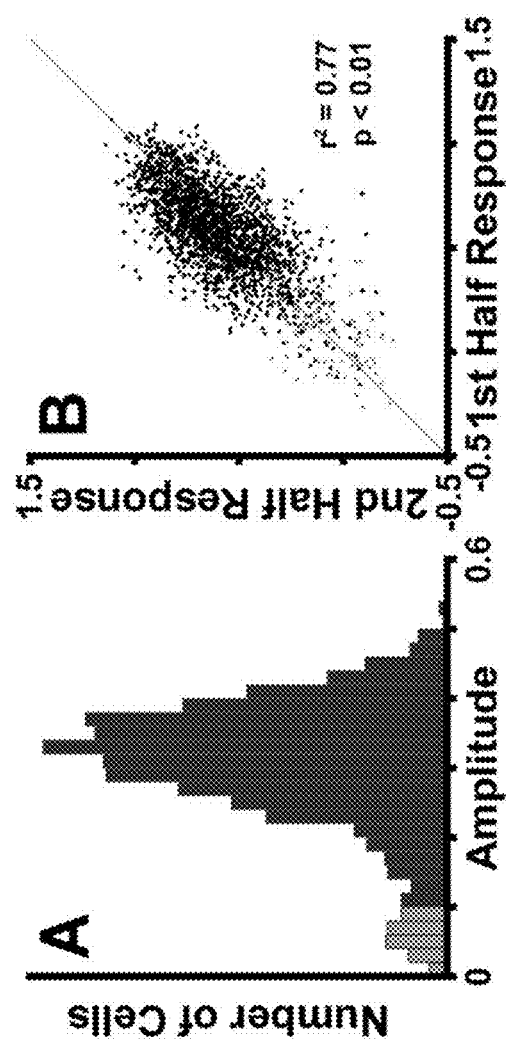
FIG. 16A
FIG. 16B
FIG. 16C
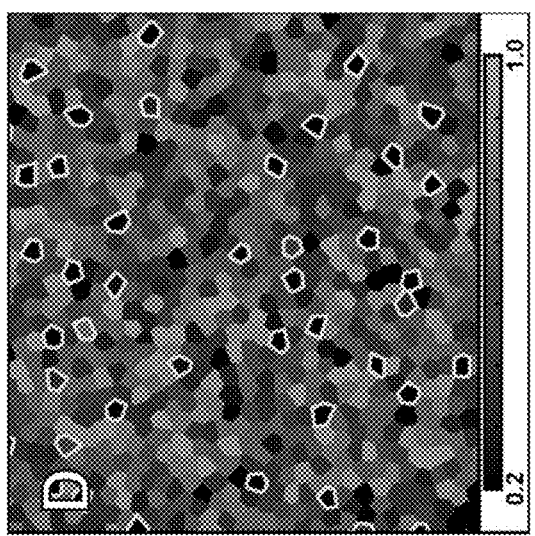
FIG. 16D

METHODS AND SYSTEMS FOR ASSESSING PHOTORECEPTOR FUNCTION

CROSS REFERENCE TO RELATED APPLICATIONS

This application claims priority to U.S. Provisional Application No. 62/660,868 filed Apr. 20, 2018. This application is incorporated herein by reference.

STATEMENT REGARDING FEDERALLY SPONSORED RESEARCH OR DEVELOPMENT

This invention was made with government support under Grant No. U01 EY025477 awarded by the National Institutes of Health. The government has certain rights in this invention.

BACKGROUND OF THE INVENTION

Vision begins when light isomerizes the photopigments within photoreceptors. To date, researchers and clinicians have traditionally relied on functional assessments of vision and photoreceptor function (e.g., such as visual acuity, visual fields, microperimetry, and electroretinograms) for the diagnosis, treatment, and prognosis of retinal disease. These techniques are sensitive only for examining the function of a large area of retina. While these techniques are sensitive to substantial photoreceptor loss, they have insufficient resolution to discern functional changes on the scale of individual cones and/or rod photoreceptors. In some instances, they combine signal from hundreds of photoreceptors into a single functional measure. This represents a significant gap in current ophthalmic assessment capabilities, as the need for more accurate assessment is crucial to current therapeutic approaches. Such approaches, including optigenetic, gene, molecular, and stem cell therapeutic approaches, attempt to treat blinding retinal degenerations by restoring function to individual retinal cells, in particular, the photoreceptors.

Noninvasive cellular-scale observation of the structure of the human photoreceptor mosaic is made possible through the use of retinal imaging with adaptive optics (AO) enhanced ophthalmoscopes. Retinal imaging with adaptive optics (AO) has enabled noninvasive visualization of cone structure both in health and disease for over two decades. AO-enhanced ophthalmoscopes have the resolution necessary to observe the human photoreceptor mosaic at a cellular scale[1-4] but are currently used primarily to analyze the structural arrangement of photoreceptors. While quantifying the structure of the cone mosaic is one approach to evaluating photoreceptor integrity, functional correlates at such fine scale structure are difficult to establish with conventional tests of visual function[5-8]. Establishing noninvasive objective measures of photoreceptor function on a similar scale has been more difficult.

Ophthalmoscopes enhanced with adaptive optics or other aberration correcting technology have demonstrated the resolution necessary to observe the structure of individual cone photoreceptors. Current ophthalmoscopes, and even those enhanced for higher resolution imaging, detect structural abnormalities (without the ability to determine function). However, the observation of cone structure through these imaging systems does not indicate the extent to which a cone cell functions.

Studies that assess cone function using AO remain sparse. Recently, near-infrared AO ophthalmoscope images obtained from the human eye have shown that cone photoreceptor reflectance[9-11] and optical path length[12] change in response to a visible stimulus. The origin of this stimulus-evoked change in cellular reflectance is not known; one hypothesis is that the intrinsic response arises from subtle morphological/biophysical changes in cones induced by isomerization of cone photopigment[9, 13]

Despite the use of AO ophthalmoscopes ability to measure these reflectance and optical path length changes, the significance of such changes remains unknown.

SUMMARY OF THE INVENTION

As disclosed herein, methods and systems are described to provide new and effective tools and methods for cellular-scale measurement of visual function and correlation of such measurements to blinding diseases and/or treatment efficacies.

In one aspect, a method for assessing photoreceptor function comprises stimulating a change in a subject's photoreceptor by exposing the subject's eye to a visible light stimulus; imaging the intrinsic reflectance response arising from the stimulus; and identifying a pattern of change in the intrinsic reflectance response indicative of an ocular disease, disorder or response to treatment for said ocular disease or disorder.

In another aspect, a method for non-invasive assessment of photoreceptor function in a mammalian subject comprises: exposing a subject's eye to a visible light stimulus, wherein absorption of visible light by photoreceptor photopigment initiates an intrinsic reflectance response; imaging the variability in the photoreceptor's intrinsic reflectance in response to the stimulus; and identifying a pattern of variability or variation in the intrinsic reflectance response indicative of an ocular condition, disease, disorder or a response to treatment for said ocular condition, disease or disorder.

In still another aspect, a method for non-invasive assessment of the function of a single photoreceptor in a mammalian subject comprises exposing a subject's eye to a visible light stimulus, wherein absorption of visible light by photoreceptor photopigment initiates an intrinsic reflectance response and capturing multiple images of a single photoreceptor's intrinsic reflectance response to the stimulus. This process can be conducted in parallel on many individual photoreceptor(s) simultaneously. The exposing and capturing steps are repeated as trials for the single photoreceptor using different light stimulus wavelengths, intensities, and intervals to obtain multiple reflectance traces of the single photoreceptor. The resulting data points forming each photoreceptor reflectance trace or trial are normalized and standardized. The mean change in photoreceptor reflectance and variability of reflectance in multiple traces/trials is obtained. A pattern of variability in the intrinsic reflectance response is detected using standard deviation and median deviation and PCA analysis of the data. The resulting pattern of variability in intrinsic reflectance of a single photoreceptor is indicative of an ocular condition, disease, disorder or a response to treatment for said ocular condition, disease or disorder. In still other aspects, these methods are computer-implemented or employ computer programs that perform the required calculations as part of the exposing and image capturing methods.

In another aspect, an apparatus comprises an adaptive optics-enhanced ophthalmoscope, a light source for applying visible light stimulus to initiate an intrinsic reflectance response in a subject's eye; and a computer program directing the wavelength, intensity, and timing of the stimulus application and the timing of imaging the variability in the photoreceptor's intrinsic reflectance in response to the stimulus for a non-invasive assessment of photoreceptor function.

Still other aspects and advantages of these compositions and methods are described further in the following detailed description of the preferred embodiments thereof.

BRIEF DESCRIPTION OF THE DRAWINGS

FIGS. 1A to 1F illustrate the steps taken to determine which cones were included for reflectance analysis. FIG. 1A shows that the average image (cropped to 113×113 μm [~0.4×0.4°] for visualization) from the top half of a stimulus trial's image sequence, with overlaid cone locations. For each image sequence, we created a map of the extent of the stimulus delivered to the photoreceptors (FIG. 1B), shaded to indicate the percentage of the total stimulus that was delivered to each retinal region. Lighter shading corresponds to a delivery of a greater percentage of the stimulus. Cones that received greater than 90% of the stimulus were categorized as 'stimulated' cones; cones that received less than 90% of the stimulus (dashed line) were excluded from analysis. FIG. 1C is a map of the categorized cone locations. White points label stimulated cones and black points label excluded cones. After the cells were categorized, a motion contrast image (FIG. 1D) was generated using Tam et al.'s algorithm[22]. The motion contrast image was thresholded to create a mask (FIG. 1E) of the capillaries present in the image. FIG. 1F is the mask used to further exclude cones (additional black points) underlying capillaries. The remaining stimulated cones (white points in FIG. 1F) were used in subsequent analyses. Scale bar is 30 μm.

FIGS. 2A-2F show the pre-processing steps used to standardize each cone's reflectance. Raw cone reflectance signals were extracted from each included cone for the control (FIG. 2A, 569 cones) and stimulated (FIG. 2D, 675 cones) image sequences. For visualization here, we display each cone's reflectance signal relative to its starting value. To remove the effect of frame-to-frame changes in image intensity, each cone's reflectance was scaled by the mean cone reflectance at each time point for the control (FIG. 2B) and stimulated image sequences (FIG. 2E). As in (FIG. 2A) and (FIG. 2D), each cone's reflectance signal is relative to its starting value for visualization only. (FIGS. 2C and 2F). Finally, individual cone reflectance signals were standardized to their pre-stimulus behavior by subtracting each cone's pre-stimulus mean from itself, then dividing by its pre-stimulus standard deviation. Stimulus duration indicated by the black bars.

FIG. 3A is a 58×58 μm cropped section of an image of the cone mosaic exposed to a two-second, 390 nW/degree$^2$ (2.2·10$^4$ cd/m$^2$) 550 nm stimulus in subject 11015. FIG. 3B shows that cones' reflectance signals responded to the stimulus in a highly variable manner. Some cones increased their reflectance (solid line profile) in response to the stimulus, others decreased their reflectance (dashed line profile), and some oscillated (dotted line profile). FIG. 3C shows that the reflectance response of a single cone was also heterogeneous across trials. While the reflectance in the first trial increased (profile 1), following trials decreased (profile 5), increased (profiles 2, 4), and showed minimal to no change (profile 3). Stimulus duration indicated by the black bar. Scale bar is 15 μm.

FIG. 4A shows that repeat control and stimulated trials show a clear, measurable and reliable intrinsic reflectance response. The baseline is centered at 1 because Eq. (2) standardizes the response to the mean and standard deviation of the stimulus behavior. FIG. 4B shows that all trials for a given condition were then combined using pooled standard deviation, and the stimulus-evoked intrinsic reflectance response was taken as the difference between the stimulated and control pooled standard deviations. Signal gaps correspond to frames within each image sequence where the cone reflectance could not be measured due to failed registration (e.g. resulting from blinks or excessive eye motion). Stimulus duration indicated by the black bar. Data shown are from subject 11015 using a 550 nm, 337 nW/deg$^2$ stimuli.

FIG. 5A shows the reflectance response as a function of time for four stimulus intensities, overlaid with piecewise function fits (dotted lines; Equation (3) as identified in Example 1 below). The reflectance response amplitude was extracted from each function by subtracting the mean prestimulus value from the peak fit value. As the intensity of the stimulus increased, the amplitude of the response also increased. Moreover, a more intense stimulus appeared to cause the peak of the intrinsic response to occur earlier in time with a steeper response slope. Stimulus duration indicated by the black bar. FIG. 5B shows the reflectance response amplitudes from FIG. 5A as a function of stimulus intensity. Data shown are from subject 11015 using 550 nm stimuli. Error bars delineate the 5th through the 95th percentile of the bootstrapped values.

FIG. 6A is a graph for subject 11002 in which the order of wavelength for the curves going from left to right is 550 nm, 510 nm, 590 nm, 480 nm and 675 nm. FIG. 6B is a graph for subject 11015 in which the order of wavelength for the curves going from left to right is 550 nm overlaying 590 nm, 510 nm, 480 nm and 675 nm. The graph of FIG. 6C for subject 11043 has the order of wavelength for the curves going from left to right as 550 nm and 510 nm overlaying each other; 590 nm, 480 nm and 675 nm. The graph of FIG. 6D for subject 11046 has the order of wavelength for the curves going from left to right as 550 nm, 590 nm, 510 nm, 480 nm and 675 nm. The graph of FIG. 6E for subject 11049 has the order of wavelength for the curves going from left to right as 510 nm, 550 nm, 590 nm, 480 nm and 675 nm. To determine the action spectrum for each subject, we fit the amplitude-irradiance functions across all wavelengths using a sigmoid with a common amplitude and slope, but unique shifts along the abscissa for each wavelength. The fit derived for each subject and each wavelength (dashed lines) is overlaid on each subjects' amplitude response. Displayed data points were obtained from each condition's pooled reflectance response. Error bars delineate the 5th through the 95th percentile of the bootstrapped amplitude distribution.

FIG. 7A shows that for each subject, the horizontal shifts of the sigmoid fits for each wavelength relative to the 550 nm fit were taken as the relative action. To assess the variability of the amplitude responses and the sigmoidal fits, we bootstrapped each reflectance response, extracted the reflectance response amplitudes and repeated the fitting process 1,000 times. Error bars delineate the 5th through the 95th percentile of the bootstrapped values. In cases where error bars are not visible, they are smaller than the plotted points. FIG. 7B shows the average (across subjects) action spectrum of the intrinsic reflectance response (points with error bars) overlaid on the human luminosity function (black dashed line). Overall, the action spectrum of the intrinsic reflectance response is well-matched to the photopic luminosity function. Error bars are ±2 standard deviations.

FIG. 10 is a table of reflectance response amplitudes averaged over all trials of a stimulus condition for each subject.

FIG. 11A measures at 675 nm wavelength. FIG. 11B measures at 550 nm wavelengths. These data matched in irradiance and wavelength but not retinal location.

FIG. 12A measures at 675 nm wavelength. FIG. 12B measures at 550 nm wavelengths. Four CHM and 5 healthy controls matched for wavelength, intensity and retinal location.

FIGS. 14A-14C shows reflectance response measured for the four individual cones indicated by boxes on the photoreceptor mosaic image (A). NIR cone reflectance in response to visible-light stimulation (stimulus duration shown by gray bars) is heterogeneous across cones (B,) and is also heterogeneous across trials for a single cone (C, cone noted, 40 individual trials). The black trace (C) shows the across-trial reflectance response for the cone outlined; the log reflectance response amplitude for this cone is 0.64.

FIGS. 15A and 15B show reflectance response of stimulus intervals versus control intervals (A) of >1,900 cones (each dot is a single cone's response) for a 545 nm, 900 nW/deg2, 1 s stimulus. Grey points show cones preliminarily identified as S cones. S cones would not be stimulated by 545 nm light. The reflectance response measured by pooling signals from each cone with its 2 nearest neighbors (B), shows 100% discriminability between stimulated and control interval responses.

FIGS. 16A-16D show candidate S cones, identified as cones with densitometry amplitude of <0.1 (FIG. 16A), colored grey. AO densitometry methods for identifying S cones have been previously described. Reflectance responses both within (FIG. 16B) and across (FIG. 16C) sessions are correlated. Each data point in FIG. 16B and FIG. 16C corresponds to the log reflectance response of a single cone. Grey data points correspond to S cones identified in FIG. 16A. For FIG. 16B, data from 50 trials for each cone were randomly split in half, with each half analyzed separately. For FIG. 16C, 50 trials were collected in each of two independent imaging sessions. Note that candidate S cones repeatedly show low reflectance responses, as would be expected for 545 nm stimuli. Psuedocolored mosaic (FIG. 16D) shows the log reflectance response of individual cones, with S cones identified by AO densitometry outlined in white.

DETAILED DESCRIPTION

Figure 3C:
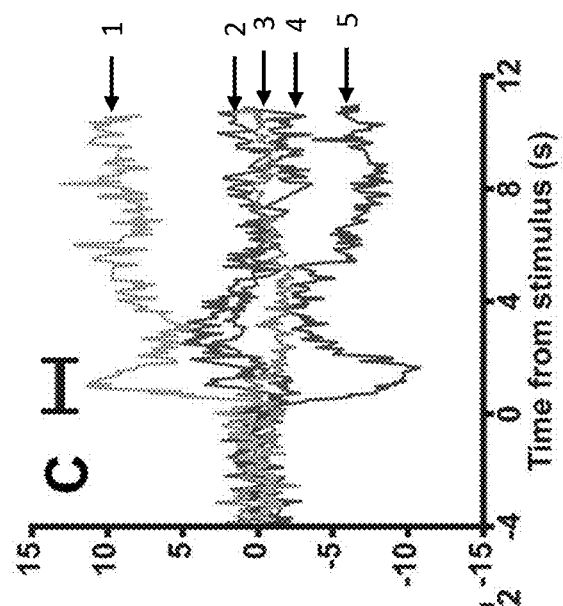
FIGS. 3A-3C show individual infrared cone reflectance responds idiosyncratically to visible light stimulation.

The methods, tools and techniques described herein are based upon the discovery that a detectable signal or pattern or profile useful in the diagnosis, treatment or monitoring of therapy can be generated by generating a physical change in the photoreceptor cells (e.g., rods and cones) of the eye in response to a visible light stimulus, i.e., the intrinsic change in reflectance over a population of photoreceptors or in a single photoreceptor. This reflectance response to visible light stimulus (e.g., irradiance) is demonstrated to be robust, quantifiable and repeatable. Further, the inventors established that the reflectance response follows known properties of the visual system. The methods permit non-invasive measurement of an objective functional response from individual photoreceptors in the living human retina. These methods permit the quantifying of the changes that photoreceptors exhibit in their reflectance of infra-red light, when exposed to a visible light stimulus.

The inventors have developed an image acquisition and analysis procedure that directly measures multiple photoreceptors' functional responses simultaneously while still maintaining high spatial resolution, even at the individual cellular level. The intrinsic response depends on stimulus wavelength and intensity, and its action spectrum is well-matched to the spectral sensitivity of photoreceptor-mediated vision. The data provided in the examples below demonstrate that the photoreceptor reflectance response is mediated by photoisomerization, thus making it a direct measure of photoreceptor function. The analysis methods allow pooling together of photoreceptor signals to obtain functional measurements of a group of photoreceptors (similar to a multi-focal ERG) or to assess individual photoreceptor function. In addition, the technology provides an alternative solution for high-spatial resolution assessment of photoreceptor function. As described herein, the inventors have demonstrated that this change in reflectance can be quantified with the spatial resolution of a single photoreceptor. The methods described herein also enable structure/function studies at the single photoreceptor scale. Such methods are useful in evaluation of patients with ocular disease, and in tracking the efficacy of treatments where photoreceptor function is desirably measured at or near the single photoreceptor scale. These methods are also valuable as research tools for the study of basic function in healthy subjects.

Specifically, the magnitude of the reflectance response increases with stimulus irradiance and its action spectrum matches the spectral sensitivity of the eye (the human photopic luminosity function). Moreover, as shown below in the Examples, preliminary data from patients with reduced retinal sensitivity also show a decreased reflectance response. These data provide evidence that the methods and tools described herein manipulate the reflectance response for use as a biomarker for assessing photoreceptor function with high resolution.

The methods also possess the ability to quantify the change in reflectance with the spatial resolution nearing that of a single photoreceptor through normalization of the response over repeated measures. The near infra-red photoreceptor reflectance response provides a measure of photoreceptor function. The response is localized to individual photoreceptors, with current signal to noise ratio approaching single photoreceptor resolution.

Example 1 demonstrates that the intrinsic (functional) reflectance response for a photoreceptor population is dependent on stimulus irradiance and wavelength and is related to photoreceptor phototransduction. Additionally, Examples 2-5 demonstrate that the acquisition and analysis procedures are useful to directly measure the intrinsic response of single photoreceptors in the living human eye. Examples 7-9 demonstrates cone reflectance response increases with stimulus irradiance or longer coherence length.

Definitions and Components of the Methods

Technical and scientific terms used herein have the same meaning as commonly understood by one of ordinary skill in the art to which this invention belongs and by reference to published texts, which provide one skilled in the art with a general guide to many of the terms used in the present application. The definitions contained in this specification are provided for clarity in describing the components and compositions herein and are not intended to limit the claimed invention.

"Patient" or "subject" as used herein means a mammalian animal, including a human, a veterinary or farm animal, a domestic animal or pet, and animals normally used for clinical research, including without limitation, humans, dogs, cats, or other domesticated animals, horses, livestock, laboratory animals, including non-human primates, etc. The subject may be male or female. In one embodiment, the subject is a human.

"Photoreceptors" are cells in the retina that absorb and convert light into electrical signals. These signals are sent to other cells in the retina and ultimately through the optic nerve to the brain where they are processed into the images. There are two general types of photoreceptors, called rods and cones. "Cone Photoreceptors" or "Cones" are a photoreceptor cell located in the retina, primarily in the macula, of mammalian eyes, that are responsible for color vision. Cones are concentrated in the fovea centralis. They are responsible for both color vision and high visual acuity. Cones reside mostly in the central portion of the retina and allow us to perceive fine visual detail and color. "Rod Photoreceptors" or "Rods" are a photoreceptor cell found concentrated at the outer edges of the retina of mammalian eyes, that are responsible for vision in less intense light. Rods are usually used in peripheral vision. Unless specified otherwise in this specification, the term "photoreceptor" refers to rods or cones. The methods described herein are applicable to both types of photoreceptor.

"Intrinsic reflectance response" as used herein means changes in scattered infrared light reflected from a photoreceptor in response to a visible light stimulus. This scattered infrared light may be captured by a high-resolution imaging device to allow its localization to individual photoreceptors.

By the term "image" as used herein includes a high resolution photograph, or data converted to quantifiable numerical information on a graph or table, or other numerical data, as shown in the figures herein and known to one of skill in the art.

"Visible light stimulus" as used herein means the portion of the electro-magnetic spectrum that is visible to the human eye. A typical human eye will respond to wavelengths from about 390 to 700 nm, e.g., 440 nm, 510 nm, 550 nm, 600 nm, 675 nm and 700 nm, including wavelengths between each of these values. Electromagnetic radiation in this range of wavelengths is called visible light or simply light. For use in the methods described herein the light stimulus may be any wavelength within this range. As described herein the methods employ visible light stimuli to cause a change in the infrared light reflected from a photoreceptor. According to the methods herein, the photoreceptors are stimulated with varying different wavelengths, intensities and durations of visible light stimuli and the resulting changes in intrinsic reflectance are imaged and found useful in providing information on photoreceptor function. In one embodiment, the light stimulus is a coherent light source. In another embodiment, the light stimulus is a partially-coherent light source.

"Infrared light" or "Infrared" refers to wavelengths of light above about 750 to about 1100 nm. The term "near infrared" refers to light that overlaps the visible light spectrum and infrared light wavelengths.

"Standard" or "Control" as used herein refers in one aspect to the intrinsic reflectance of a photoreceptor which is measured prior to exposure to a visible light stimulus. The "reference standard" is preferably provided by using the same technique as is used for measurement of the subject's intrinsic photoreceptor reflectance in the reference subject or population, to avoid any error in standardization. A reference standard is, alternatively, a numerical value, a predetermined cutpoint, a mean, an average, a numerical mean or range of numerical means, a numerical pattern, a ratio, a graphical pattern or a profile or activity level profile derived from the same photoreceptors in a reference subject or reference population.

"Reference or Control subject" or "Reference Population" defines the source of the reference standard. In one embodiment, the reference is a human subject or a population of subjects having no ocular disease, i.e., healthy controls or negative controls. In yet another embodiment, the reference is a human subject or population of subjects with an ocular disease characterized by visual impairment. In yet another embodiment, the reference standard is a subject or population with one or more clinical indicators of retinopathy. In still another embodiment, the reference is a human subject or a population of subjects who is being treated for a retinopathy. Similarly, in another embodiment, the reference is a human subject or a population of subjects following therapeutic treatment for an ocular disease or condition. In still another embodiment, the reference is a human or a population of subjects receiving or being monitored for efficacy of treatment. In still another embodiment, the reference is a human subject or a population of subjects prior to therapeutic treatment of an ocular disease or disorder. In still other embodiments of methods described herein, the reference is a temporally earlier intrinsic reflectance profile obtained from the same subject. In another embodiment, the reference standard is a combination of two or more of the above reference standards.

Selection of the particular class of reference standards, reference population, biomarker profiles depends upon the use to which the diagnostic/monitoring methods and are to be put by the physician and the desired result, e.g., initial diagnosis of an ocular disorder, evaluation of the efficacy of therapeutic protocols, clinical management of patients with an ocular disorder, e.g., after initial diagnosis, including, but not limited to, monitoring for reoccurrence of disease or monitoring remission or progression of the disease, selecting among therapeutic protocols for individual patients (e.g., predicting the suitability of treatment), monitoring for development of toxicity or other complications of therapy, predicting development of therapeutic resistance, and the like.

By "ocular disease, disorder or condition" as used herein includes, without limitation, retinitis pigmentosa, Choroideremia, rod-cone dystrophy, Leber's congenital amaurosis, Usher's syndrome, Bardet-Biedl Syndrome, Best disease, retinoschisis, Stargardt disease (autosomal dominant or autosomal recessive), untreated retinal detachment, pattern dystrophy, cone-rod dystrophy, achromatopsia, ocular albinism, enhanced S cone syndrome, diabetic retinopathy, age-related macular degeneration, retinopathy of prematurity, sickle cell retinopathy, Congenital Stationary Night Blindness, glaucoma, or retinal vein occlusion. In another embodiment, the subject has, or is at risk of developing glaucoma, Leber's hereditary optic neuropathy, lysosomal storage disorder, or peroxisomal disorder. In another embodiment, the subject is in need of optogenetic therapy. The retinal diseases described above are associated with various retinal changes. These may include a loss of photoreceptor structure or function; thinning or thickening of the outer nuclear layer (ONL); thinning or thickening of the outer plexiform layer (OPL); disorganization followed by loss of rod and cone outer segments; shortening of the rod and cone inner segments; retraction of bipolar cell dendrites; thinning or thickening of the inner retinal layers including inner nuclear layer, inner plexiform layer, ganglion cell layer and nerve fiber layer; opsin mislocalization; overexpression of neurofilaments; thinning of specific portions of the retina (such as the fovea or macula); loss of ERG function; loss of visual acuity and contrast sensitivity; loss of optokinetic reflexes; loss of the pupillary light reflex; and loss of visually guided behavior.

As one particular example of an ocular disease, Choroideremia is an X-linked inherited retinal regeneration. It is symptomatic in childhood, with symptoms such as night blindness, visual field loss initially in the periphery leading to tunnel vision; blindness in the 30-40's, although many patients maintain central vision until age 40-50. Choroideremia is caused by genetic mutations in CHM gene, which encodes Rab Escort Protein-1 (a transport protein). It is an excellent candidate for gene therapy.

The terms "a" or "an" refers to one or more. For example, "an expression cassette" is understood to represent one or more such cassettes. As such, the terms "a" (or "an"), "one or more," and "at least one" are used interchangeably herein.

The term "about" as used herein when referring to a measurable value such as an amount, a temporal duration, and the like, is meant to encompass variations of up to ±10% from the specified value; as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about."

The words "comprise", "comprises", and "comprising" are to be interpreted inclusively rather than exclusively, i.e., to include other unspecified components or process steps. The words "consist", "consisting", and its variants, when used in the claims, are to be interpreted exclusively, rather than inclusively, i.e., to exclude components or steps not specifically recited. As used herein, the phrase "consisting essentially of" limits the scope of a described composition or method to the specified materials or steps and those that do not affect significant characteristics of the described or claimed method or composition.

Methods

In one aspect, a method for non-invasive assessment of photoreceptor function in a mammalian subject comprises exposing a subject's eye to a visible light stimulus, wherein absorption of light by photoreceptor photopigment initiates an intrinsic reflectance response and capturing multiple images of photoreceptor's intrinsic reflectance response to the stimulus. These steps permit the identification of a pattern of variability or variation in the intrinsic reflectance response indicative of an ocular condition, disease, disorder or a response to treatment for said ocular condition, disease or disorder.

In one embodiment of the method, an image of the intrinsic reflectance of the photoreceptor is captured before the stimulus to establish a control or reference standard. In another embodiment, an image of the intrinsic reflectance of the photoreceptor is captured after the stimulus is applied to the eye. In still a further embodiment, the image of the intrinsic reflectance of the photoreceptor is captured during or simultaneously with the exposure of the eye to the stimulus. In still further embodiments, images are captured before, during and after exposure of the eye to the stimulus. In still other embodiments of the method, multiple, repeated trials of stimulus exposure/image capture are used. In still other embodiments, the multiple trials include uses of visible stimuli that vary in wavelength and/or intensity. In yet another embodiment, the eye is subject to darkness for a time period, followed by the stimulus, image capture and then rest or darkness, before another trial of stimulus/capture is repeated. Repetition of stimulus and image capturing may occur at repeated regular intervals or at repeated irregular intervals.

The methods described herein are not limited by the duration of the stimulus exposure, the selection of wavelength or intensity, or the time between stimulus, image capture, rest and another trial of the same steps. In embodiments other than the examples and descriptions herein, measurements may be made on multiple days, separated by days, weeks, months and/or years. In other embodiments, the duration of stimuli can vary from fractional seconds, e.g., 0.5 second through to 5 to 10 minutes or more. Similarly, the methods involve variations in wavelengths and intensity of visible light.

A profile or biomarker is provided by the method which comprises, in one embodiment, detecting a variation in intrinsic reflectance of the subject's photoreceptor between and among multiple images captured. A variation in intrinsic reflectance response can in one embodiment, be an increase in brightness of reflectance in response to the stimuli. In another embodiment, the variation is evidenced by a decrease in brightness of reflectance in response to the stimuli. In still another embodiment, a variation is evidenced by an oscillation between an increase and decrease in brightness of the reflectance. In still other embodiments of the method the intrinsic reflectance variation is a combination of two or three of these responses.

As described in Example 1, in one embodiment, this method can be applied to detect the variances in intrinsic response of a population of photoreceptors within a defined analysis area. The size of the area is not a limitation but relates to the area of the retina or macula where both the stimuli radius and imaging frame overlap to obtain consistent results. In yet another method described in more detail below, the method can obtain results from a single photoreceptor by subjecting it to multiple trials of stimuli and image capture. See, e.g., Examples 2-5.

In all of the variations of the methods described herein, exposure of the eye to visible light can be accomplished by a light or laser using one or more wavelengths in the visible light range. In one embodiment, the stimulus can be supplied by the same apparatus performing the image capture. Capturing of the image can employ known apparatus, such as an ophthalmoscope enhanced with adaptive optics or a multi-channel adaptive optics scanning light ophthalmoscopy (AOSLO). This instrument delivers visible stimuli to the retina noninvasively while simultaneously imaging the photoreceptors with infrared reflectance. Still other AO ophthalmoscopes or image capture apparatus can include a light source for applying the stimulus and/or be associated with a computer program directing the wavelength, intensity, repetition and timing of stimulus application.

In the embodiment of the methods described in the examples below, the inventors used in the examples below a custom built adaptive optics scanning light ophthalmoscope to obtain multiple image sequences of photoreceptor infra-red reflectance (>780 nm) before, during, and after delivery of a stimulus with a center wavelength in the visible spectrum (390-700 nm, hereafter referred to as a "stimulus sequence"). Multiple image sequences of photoreceptor infra-red reflectance are also acquired without a stimulus (hereafter referred to as a "control sequence"). The hardware used for data acquisition is the same illustrated in Example 1[46]. The analysis tools exemplified herein are by no means the only way to obtain the functional signals described herein.

Any existing imaging system can be employed in these methods that has sufficient resolution to observe the photoreceptor mosaic using near-infrared light, a visible stimulus that can be delivered to the photoreceptors and which encompasses the area of retina being imaged, and an analysis procedure which considers the change in a photoreceptor's reflectance profile. In some embodiments a fundus camera can be used. The methods described herein are adaptable for use with any commercial or research device capable of imaging the photoreceptors, including the "RTX1" adaptive optics ophthalmoscope from Imagine Eyes, or systems available from Physical Sciences Inc., Boston Micromachines Corporation and Canon. In certain embodiments, the instrument can be computer-implemented to provide the instrument with instructions and patterns to turn both the stimulus and image capture functions on and off at set intervals.

Still another aspect of the methods involves detection and analysis of the variations in intrinsic reflectance. Thus, in another embodiment, the methods described above further incorporate a step of quantifying the stimulus-evoked variability in the images by correcting for changes in image intensity in the width of the image frame. Such a method step uses, in one embodiment, the function shown in Equation (1) of Example 1. Yet another method step involves evaluating the intrinsic reflectance data by removing stimulus-independent source of variation. In one embodiment, this can be done by use Equation (2) as shown in Example 1. Yet a further analytical manipulation involves quantifying the intrinsic reflectance response. In one embodiment, this can be accomplished by using Equation (3) as described in Example 1. In yet another embodiment, the detection of the profile involves determining the action spectrum of reflectance response for each subject. In one example, this is done by use of Equation (4), described in detail in Example 1 below. Still other methods of quantifying the intrinsic reflectance response may include steps for noise removal and response extraction. Other modifications that are refinements of the methods described herein are intended to be included, as modifying step can be selected by the person of skill in the art given the teachings provided herein.

In still another aspect, the methods described above can include a step of classifying photoreceptors according to the condition of the subject, e.g., healthy or having an ocular disease, or being treated for an ocular disease, as detailed herein. A photoreceptor population response can be identified by pooling intrinsic reflectance responses with an image frame of a selected dimension for each condition. Such frame dimensions are not a limitation of these methods and can be selected by the person of skill in the art.

Employing one or more of these methods of evaluation, a pattern of variations in intrinsic reflectance responses is produced by the method, which can be used as a biomarker for an ocular disorder, such as any of those listed above. One exemplary embodiment includes a retinopathy. Another example shown in the examples below to which the methods are applied is Choroideremia. In still another method, the pattern of variations is indicative of the condition, wherein can be used to monitor the progression of treatment of a blinding disorder.

As stated above, the parameters of these methods, including AOSLO acquisition parameters, such as the imaging light coherence length and timing of stimulus delivery, can be readily changed or optimized to maximize the reflectance response.

In yet another aspect, the methods described herein can be specifically adapted to measuring intrinsic reflectance functional signals of individual photoreceptors. In one embodiment a method for non-invasive assessment of the function of a single photoreceptor in a mammalian subject comprises exposing a subject's eye to a visible light stimulus, wherein absorption of light by photoreceptor photopigment initiates an intrinsic reflectance response; capturing multiple images of a single photoreceptor's intrinsic reflectance response to the stimulus; and repeating successively exposing and capturing trials for the single photoreceptor using different light stimulus wavelengths, intensities, and intervals to obtain multiple photoreceptor reflectance traces of the single photoreceptor. Such a method can employ the apparatus and instruments described herein for evaluating a population of photoreceptors. The multiple trials or each photoreceptor reflectance traces generated by the trials are normalized and standardized. In one embodiment, the methods employing Equations (1) and (2) of Examples 1 and 3 can be used for this purpose.

In still another embodiment, the method can include a step of obtaining the mean or median change in photoreceptor reflectance and variability of reflectance in multiple traces. One embodiment of this step is provided in Example 3. Thereafter, a pattern of variability in the single photoreceptor's intrinsic reflectance response is identified as indicative of an ocular condition, disease, disorder or a response to treatment for said ocular condition, disease or disorder.

Yet a further embodiment of this method involves obtaining photoreceptor standardized photoreceptor reflectance signals at each time point t for all stimulus trials and calculating the standard deviations thereof to obtain a photoreceptor standard deviation profile. In another embodiment, the method involves obtaining photoreceptor standardized photoreceptor reflectance signals at each time point t for all stimulus trials and calculating the median at each time index of a photoreceptor's reflectance profile across all of its stimulus trials to obtain a photoreceptor median profile. In still additional embodiments, the method for identifying the variations in reflectance in the single photoreceptor further comprises performing a principle component analysis (PCA) on the photoreceptor profile, wherein the reflectance response for the single photoreceptor is derived from the PCA score. An example of this step is also described in detail in Example 3. Other embodiments of this method employ one or combinations of a photoreceptor standard deviation profile and a photoreceptor median profile, or either profile from which control values have been subtracted.

In still additional embodiments, these methods extract different aspects of the intrinsic reflectance response signal profiles, such as their latency, rate of change or peak. These aspects of the intrinsic reflectance response may be processed to form an additional or alternative response measures. Different choices of how to extract, process and combine various response measures from the signals are modifications of the methods believed to be encompassed by this specification. Such modifications of the methods given these teachings are believed to be selected by the person of skill in the art given the teachings supplied by the specification In still further embodiments of the various methods described herein, one of more of these analysis steps may be computer-implemented, i.e., may be directed by a computer program directing use of the equations referenced herein.

In one specific description, the single photoreceptor analysis method is performed as follows. Once the data is captured, we co-align all image sequences to obtain photoreceptor-to-photoreceptor (e.g., cone to cone) correspondence and determine the locations. We exclude photoreceptors underlying retinal capillaries. A reflectance profile (reflectance vs time) is created for each photoreceptor by first projecting a 3×3 pixel column through the aligned image sequence at each photoreceptor location and then averaging the 9 (3×3) pixels in each frame. For each frame in the image sequence, a photoreceptor's reflectance is divided by the mean reflectance of all photoreceptors (e.g., cones) in that frame. Each intrinsic reflectance profile is then standardized with respect to its own prestimulus mean and standard deviation (Examples 1 and 2 below). We exclude stimulus and control sequences for a particular photoreceptor if the photoreceptor does not have a reflectance signal for 90% or more of the time period corresponding to stimulus delivery within that sequence. Currently, we further exclude photoreceptors that reach the end of the data processing pipeline with reflectance profiles from fewer than 25 stimulus and control sequences. The exact parameters of the image acquisition and processing are not crucial and are likely to be refined. The invention should be considered to include future refinements of the details.

As one specific example, we determine the functional response of a single cone photoreceptor as follows. We first calculate the cone's standard deviation (defined as the square root of the variance) of its reflectance profiles across all stimulus and control sequences independently. Then we subtract the standard deviation of each cone's control sequences from the standard deviation of its stimulus sequences at each time point. We fit a piecewise smooth function (as in Example 1) to the time course of each cone's reflectance response and determine its peak amplitude. This is the standard deviation cone intrinsic reflectance response. In addition, we determine the mean intrinsic reflectance response of each cone, by calculating the cone's mean reflectance profile for stimulus and control sequences independently. We subtract the mean of each cone's control sequences from the mean of its stimulus sequences at each time point and fit the result with the same piecewise smooth function as used for the standard deviation cone intrinsic reflectance response. The final intrinsic reflectance response for each cone is a combination of the peak amplitudes from the fits for the mean and standard deviation cone reflectance responses. Currently, the combination is done by adding the standard deviation-based reflectance response fit peak amplitude to the absolute value of the mean intrinsic reflectance response fit peak amplitude. As with the image processing description above, this processing method is one of several related methods. For example, variations in the functional form with which we fit the response, as well as the addition of pre-processing to reduce noise in the data and different methods for combining multiple aspects of the response, are modifications that may improve the performance of the method described herein. This same protocol can be followed with rods, rather than cones.

In yet other embodiments, the methods described herein can be designed for performance by a custom apparatus. In one embodiment such an apparatus comprises an adaptive optics-enhanced ophthalmoscope, a light source for applying visible light stimulus to initiate an intrinsic reflectance response in a subject's eye; and a computer program directing the wavelength, intensity, and timing of the stimulus application and the timing of imaging the variability in the photoreceptor's intrinsic reflectance in response to the stimulus for a non-invasive assessment of photoreceptor function. In still another embodiment, the tool can be a computer or computer system designed to implement the specific instructions as to directing the wavelength, intensity, and timing of the stimulus application and the timing of imaging, as well as to implement the various equations and features of the analytic methods applied to the images.

The methods and tools described herein are useful in ophthalmology clinics as an objective assessment of photoreceptor function. The analysis methods allow pooling together of photoreceptor signals to give functional measurements of a group of photoreceptors (similar to a multifocal ERG) or to assess individual photoreceptor function. In addition, the methods described herein permit high-spatial resolution assessment of photoreceptor function. Specifically, these methods are useful to assess the safety and efficacy of experimental therapies in clinical trials, such as retinopathy clinical trials, or the effectiveness of non-experimental therapies that are delivered to a patient in the clinic. These methods can supplement, or possibly replace some uses of, the electroretinogram and potentially allow early diagnosis due to its better sensitivity. As with other functional assessments of vision, these methods involving the functional assessment of photoreceptors aids in the diagnosis of retinal disease and determines the prognosis for photoreceptor health. This technology is a more sensitive and proximal biomarker of visible function and treatment response. Access to such a biomarker method for directed at rapid evaluation of the photoreceptor status will assist the development and testing of novel retinal therapeutics aimed at restoring photoreceptor function.

This method is much higher in resolution than results obtained from an electroretinogram. These methods are more accurate in identifying how many photoreceptors contribute to the measured signal, i.e., a smaller number of photoreceptors means higher resolution because the signal can be ascribed to a more localized region of the retina.

The following examples disclose specific embodiments of the methods described herein and should be construed to encompass any and all variations that become evident as a result of the teaching provided herein.

Example 1: Non-Invasive Assessment of Human Photoreceptor Function

We developed a method to extract clear, reliable, and quantifiable intrinsic responses, to determine if stimulus-evoked changes in cone reflectance are mediated by phototransduction. We theorized that if the intrinsic reflectance response is initiated by phototransduction, it would be governed by known properties of vision.

Phototransduction begins when a photon isomerizes photopigment molecules. A characteristic signature of photopigments is their action spectrum—the relative efficiency with which incoming photons of different wavelengths cause isomerization. In the human retina, there are three spectral classes of cones, categorized by their long (L), middle (M), or short (S) wavelength sensitivities. The L and M cones predominate, comprising approximately 93% of cones in the human cone mosaic[15], with L cones outnumbering M cones by a factor of about 2:1 on average[16-18]. If we neglect the relatively small number of S cones and account for pre-retinal absorption as well as photopigment self-screening, we can characterize the visible system's overall spectral sensitivity for daylight light levels as a weighted average of the L and M cone sensitivities, where the weights are determined by the L:M ratio in the cone mosaic. This weighted average, for a typical eye, is called the phototopic luminosity function[19]. If the intrinsic reflectance response is governed by phototransduction, the action spectrum of the aggregate reflectance response should, to first order, follow the luminosity function.

Human Subjects—

This research was approved by the Institutional Research Board at the University of Pennsylvania and was conducted in accordance with the tenets of the Declaration of Helsinki. Five subjects with normal vision were recruited for this study (age range: 25-56). Subjects provided informed consent after the nature and possible risks of the study were explained. Each subjects' pupil was dilated and accommodation arrested using one drop of tropicamide (1%) and, if necessary, phenylephrine (2.5%).

Imaging the Photoreceptor Mosaic—

The photoreceptor mosaic was imaged using a previously described adaptive optics scanning light ophthalmoscope (AOSLO)[3], with a ~2 µm Rayleigh resolution. Image sequences were acquired from a photomultiplier tube using a 795 nm super-luminescent diode with a full-width at half-maximum bandwidth (FWHM) of 15.3 nm. We estimated the coherence length of the 795 nm imaging source to be 13.6 µm, assuming a cone outer segment with a refractive index of 1.43.[20] This is roughly half of the typical outer segment length (~35 µm) of cones in the retinal region that we studied[21]. Cones were stimulated using a superluminescent diode at 675 nm (Superlum Ireland; Carrigtwohill, County Cork, Ireland), and a SuperK EXTREME super-continuum laser (NKT Photonics; Birkerød, Denmark). Image sequences were obtained 0.71° from the center of fixation (0.5° temporal and 0.5° superior for four subjects, 0.5° nasal and 0.5° superior for one subject) at a rate of 16.6 frames per second, using a 1×1° field of view.

Each imaging trial consisted of two minutes of dark adaptation, four seconds of prestimulus recording, a two-second stimulus delivered to half of the imaging field (1° wide by 0.5° high), and nine seconds of post-stimulus recording, resulting in 249 images per sequence. Across trials, the stimulus was varied in both wavelength and intensity. Four of the stimulus wavelengths (480, 510, 550, 590 nm) were delivered using the super-continuum laser, with a 10 nm FWHM for 510, 550, and 590 nm wavelengths, but a 30 nm FWHM at 480 nm. The 675 nm (8.5 nm FWHM) stimulus was delivered using the super-luminescent diode. For each wavelength, we used up to four different stimulus intensities tailored to produce a range of intrinsic reflectance responses. The highest stimulus intensity at 480 nm required use of a 30 nm rather than a 10 nm FWHM and was the maximum irradiance obtainable at that wavelength. We gated stimulus delivery using an acousto-optic modulator (AOM; Brimrose Corporation, Sparks, Md., USA). We repeated each combination of stimulus wavelength and intensity (hereafter referred to as a "stimulus condition") for six trials. Even when the AOM was gated "closed", a small quantity of stimulus "leak" still passed through the system (~0.01% of the input irradiance), so that the leaked light for the nominally unstimulated condition varied with stimulus wavelength and irradiance.

We acquired two unstimulated (control) image sequences per wavelength and irradiance condition. For each control trial, the cones were illuminated with 90 µW of 795 nm imaging light combined with 8 µW of 848 nm (FWHM 26 nm) light for wavefront sensing and the leaked light for that condition.

Processing the Image Sequences—

To correct for static intra-frame distortion from the sinusoidal motion of the resonant optical scanner, we estimated the static spatial distortion after each imaging session from images of a stationary Ronchi ruling and resampled each frame over a grid of equally spaced pixels. Next, a minimally distorted frame was selected from within each of the "desinusoided" 795 nm image sequences and used as the reference frame for strip-based registration[23]. If fewer than 60% of the images within the sequence aligned (had a positive normalized cross correlation) to any reference frame, then the image sequence was removed from further consideration. 18% of the image sequences were removed in this manner, leading to an average of 4.9 trials being used for further analysis at each stimulus condition (range: 2-6). Following strip registration, a frame-wide affine registration was performed to remove residual torsion. The fully registered image sequences were cropped to a common area, and cone locations were identified[24] within an image generated from the average of all cropped frames. The results are shown in FIG. 1A.

Because the eye is constantly in motion, even for fixating subjects, cones along the border of the imaging field might not receive the full two-second stimulus. For each stimulus image sequence, we classified which cones were stimulated by determining whether the cone was within the stimulated portion of the 795 nm image sequence for at least 90% of the registered frames. See FIG. 1B. Cones that did not receive at least 90% of the stimulation as determined by this method were excluded from further analysis (FIG. 1C). For both stimulus and control image sequences, we excluded cones underlying retinal capillaries by highlighting the vasculature present within each image sequence using a modified version of a previously described algorithm (FIG. 1D)[22]. A binary mask was created from this "motion contrast" image by thresholding at a criterion defined as two standard deviations greater than the sequence's mean. See the results of FIG. 1E. Cones falling within the mask were also excluded from the analysis (FIG. 1F). On average, 665 (range: 219-1,837) cone signals were analyzed per trial.

Extracting the Reflectance Signal—

Figure 9:
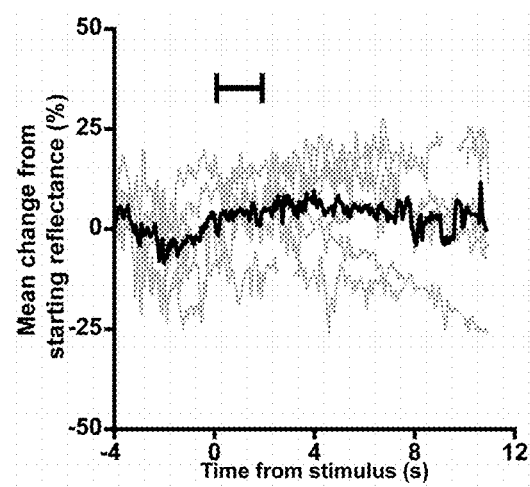
FIG. 9 is a graph showing an analysis of the mean reflectance signal content. To ensure that a mean-based intrinsic signal was not lost due our normalization approach, we examined the change in mean cone reflectance across all trials of a 550 nm, 382 nW/deg² stimulus condition for subject 11049. Individual trials (gray lines) did not show a clear, repeatable change in mean reflectance during or following the stimulus. Averaging across trials (black line) also did not produce a change in the mean.
Figure 11A:
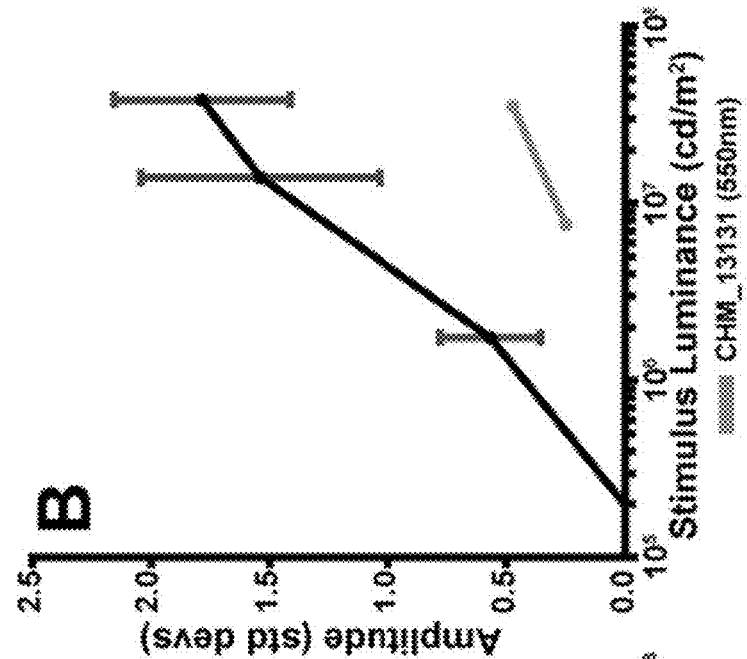
FIGS. 11A-11B are graphs showing reflectance response in a Choroideremia (CHM) patient compared to healthy controls, plotting peak response vs. stimulus luminance in cd/m². The lower line is the CHM patient.
Figure 11B:
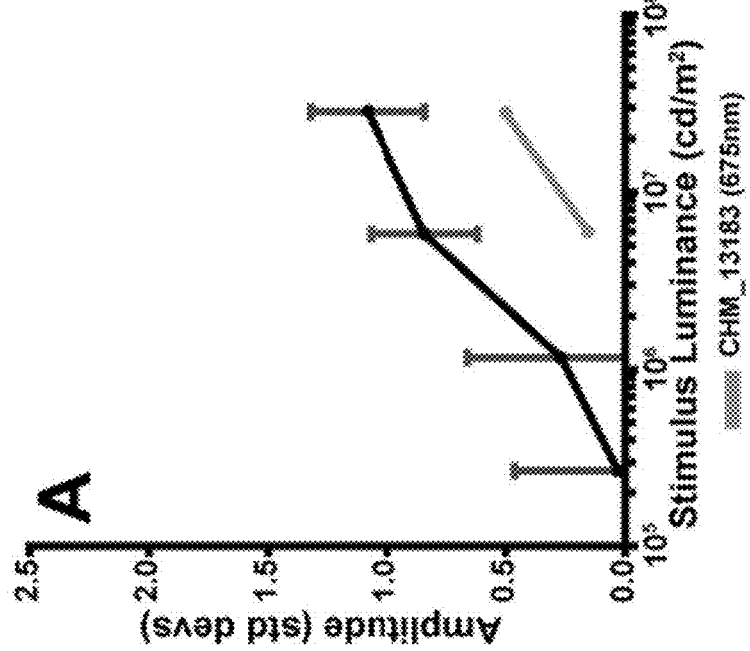
Figure 12A:
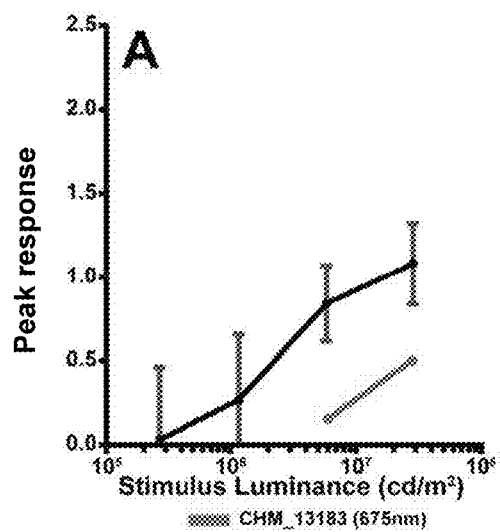
FIGS. 12A-12B are graphs showing reflectance response in Choroideremia (CHM) patients compared to healthy controls, plotting peak response vs. stimulus luminance in cd/m². The lower line is the CHM patient.
Figure 12B:
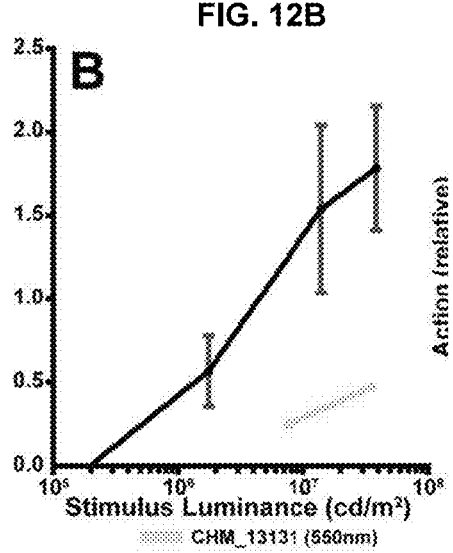
Figure 12C:
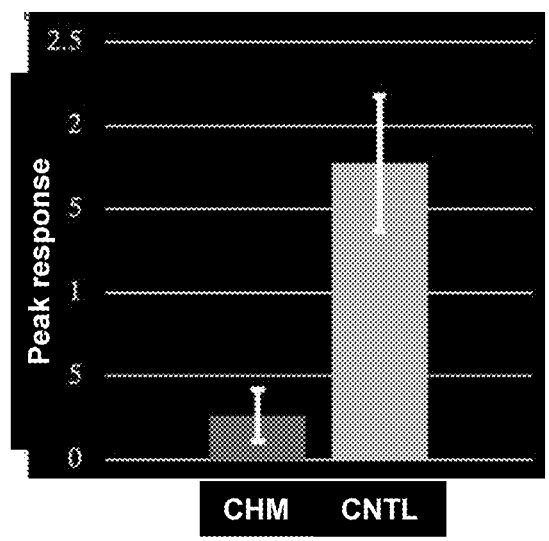
FIG. 12C is a bar graph plotting peak response vs. the CHM and Controls from the experiments of FIGS. 12A and 12B. These preliminary results demonstrate that the reflectance response can be used to measure loss of function in photoreceptors in those suffering retinopathies.
Figure 13:
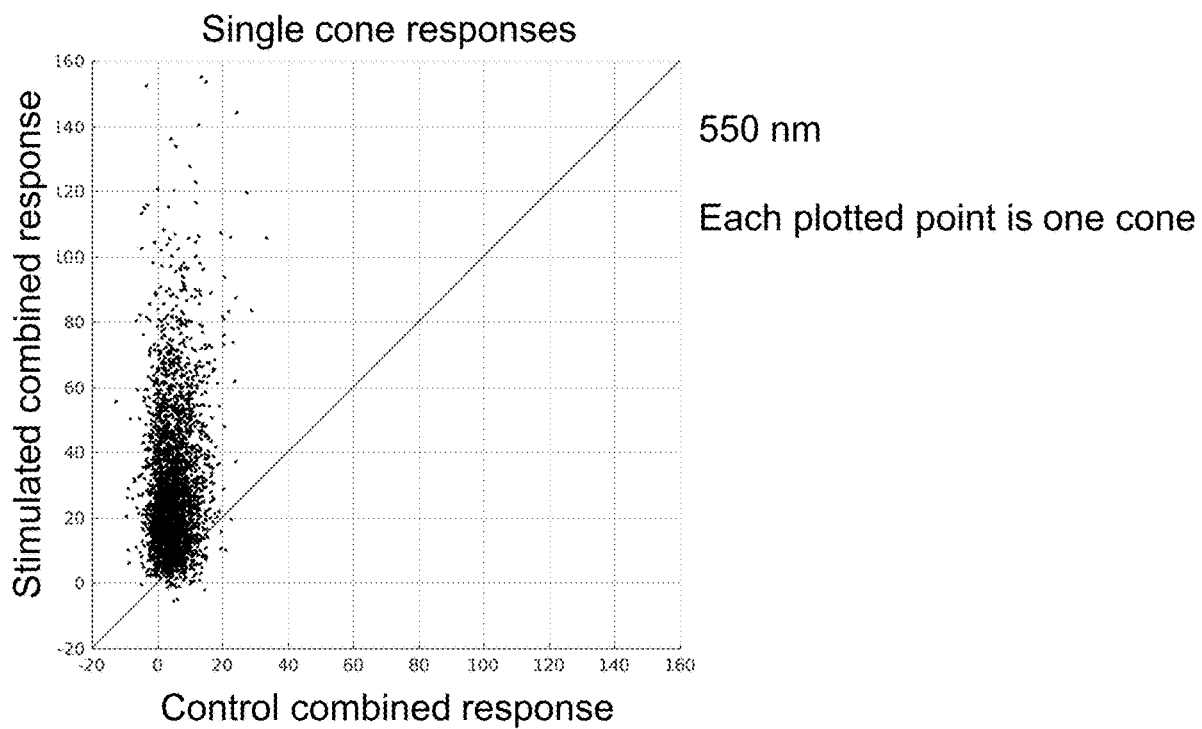
FIG. 13 is a dot plot showing single cone response reliability, which plotted stimulated combined response vs. control combined response vs. single cone responses at 550 nm. Each plotted point is one cone. About 95% of cones show increased NIR response to visible light. These data demonstrate that the NIR cone reflectance response provides a measure of cone function. The response is localized to individual cones, and our current SNR allows us to approach single cone resolution. Therefore, single cone measurements are possible.

A 2-dimensional reflectance signal (reflectance vs time) for each cone was created by first projecting a 3×3 pixel column through the aligned image sequence at each included cone location and then averaging the 9 (3×3) pixels in each frame. In a preliminary analysis (See FIG. 9), we found that the mean of the aggregate cone signals did not exhibit a stimulus-evoked change. Rather, the effect of stimulation was to increase the variability of the reflectance. To quantify the stimulus-evoked component of the variability observed in the image sequences, we adopted the process described below.

First, to correct for frame-wide changes in image intensity (due to tear film disruption, microsaccades, and changes in AO correction quality), each cone's reflectance for each frame (FIGS. 2A, 2D) was divided by the mean reflectance of the same frame of all analyzed cones, as shown in Equation (1) below:

$$R_{norm}(t)_i = \frac{R_{raw}(t)_i}{\overline{R_{raw}(t)}} \quad (1)$$

where $R_{norm}(t)_1$ is the scaled reflectance of a cone i as a function of time t, and $\overline{R_{raw}(t)}$ is the mean reflectance for the same frame of all analyzed cones (FIGS. 2B, 2E). Second, it is a well-known feature of cone reflectance images that there is cone-to-cone variation in reflectance of unknown origin[25,26]. To remove this stimulus-independent source of variation from our signals, each cone signal was standardized with respect to its own prestimulus mean and standard deviation, as shown in Equation (2) below and in FIGS. 2C and 2F:

$$R(t)_i = \frac{R_{norm}(t)_i - \overline{R_{pre_i}}}{\sigma_{R_{pre_i}}} \quad (2)$$

where $R(t)_i$ is the scaled, standardized reflectance signal from cone i as a function of time t, $\overline{R_{pre_i}}$ is the pre-stimulus reflectance mean for cone i, and $$\sigma_{R_{pre_i}}$$

is the standard deviation of the pre-stimulus reflectance of cone i.

Analyzing the Reflectance Signals—

Because we observed that the intrinsic response was heterogeneous within and across cones, we developed a statistical measure to capture a population response. We calculated the standard deviation across all cones' standardized cone reflectance signals at each time point t for each trial. The standard deviation of all control trials was subtracted from the standard deviation of all stimulated trials. This difference was taken as the measured intrinsic reflectance response, which we denote as σR(t).

For the purpose of quantifying the intrinsic reflectance response, a piecewise parametric function consisting of a gamma probability density function and an exponential decay function was fit to $\sigma_R(t)$, according to Equation (3) below:

$$\sigma_{fit}(t) = \begin{cases} \frac{A_\Gamma}{\Gamma(k)\theta^k}(t-d)^{k-1}e^{-\frac{(t-d)}{\theta}} - \overline{\sigma_{pre}}, & t < t_{\sigma_{max}} \\ \sigma_{max} + A_{exp}e^{-T(t-t_{\sigma_{max}})} - A_{exp}, & t \geq t_{\sigma_{max}} \end{cases}$$

where the fit $\sigma_{fit}(t)$ was defined by a gamma probability density function for times t less than the fit maximum $\sigma_{max}$ at time $t_{\sigma_{max}}$, and an exponential decay function for times greater than or equal to $t_{\sigma_{max}} \times \sigma_{max}$ was determined such that the upper (gamma) and lower (exponential) parts of the piecewise function maintained the same maximum value at time $t=t_{\sigma_{max}}$. To fit the signal peak, the gamma fit parameters $A_\Gamma$ (amplitude), θ (scale), k (shape), and d (delay) were allowed to vary. The value of $\sigma_{pre}$ was the prestimulus mean of the signal. To fit the signal falloff, exponential fit parameters $A_{exp}$ (amplitude) and T (decay constant) were allowed to vary. Peak amplitude was then extracted from each fit, defined as the difference between the fit maximum ($\sigma_{max}$) and the prestimulus mean.

To obtain a reasonable estimate of measurement variability, we bootstrapped the above process for each subject and condition. To create a single bootstrapped signal, we first randomly sampled with replacement the response at each time point t over all trials of a given condition N(t) times (where N(t) is the number of trials containing data at time t) for both stimulated and control image sequences. The N(t) bootstrapped samples were then combined using pooled standard deviation, and the pooled standard deviation of the control data was subtracted from the stimulated data. This bootstrapped reflectance response was fit with a piecewise function and the amplitude was extracted as described above. This process was repeated 1,000 times, creating a distribution of bootstrapped amplitudes for each subject and condition. The measurement variability was estimated from the 5th and 95th percentiles of each distribution.

Determining the Action Spectrum of the Reflectance Response—

We determined the action spectrum for each subject by fitting the amplitude-irradiance functions from each wavelength with a sigmoid function according to Equation (4) below:

$$f(E_{log_{10}}) = \frac{\alpha}{1 + e^{-\beta(E_{log_{10}} - S_w)}}$$

where $f(E_{log_{10}})$ is the sigmoid fit of the amplitude as a function of the log-irradiance $E_{log_{10}}$, $\alpha$ is the saturating amplitude, $\beta$ is the slope, and $S_w$ is the irradiance shift (on the log scale) for a given wavelength w. For each subject, five sigmoidal functions were fit simultaneously to the amplitude-irradiance functions for the five wavelengths. During fitting, a single $\alpha$ a single $\beta$ and five wavelength shifts (one $S_w$ per wavelength) were varied to obtain the best fit to the whole data set (all five measured amplitude-irradiance functions). This created a set of fit amplitude-irradiance functions for each subject with the same shape (on a log irradiance axis) across wavelengths. To obtain the action spectrum, we then calculated from the fitted amplitude-irradiance functions the irradiance shift for each wavelength relative to the 550 nm irradiance shift. To account for variability in 550 nm data, we performed a vertical shift of each subject's action spectrum on a log sensitivity axis, minimizing the root mean square error between our observed data and the human log-luminosity function.

To obtain an estimate of the variability in each action spectrum, we bootstrapped our analysis. Drawing from the distribution of amplitudes created for each subject and condition obtained through the bootstrapping amplitude analysis, we randomly selected a bootstrapped amplitude for each stimulus intensity and wavelength. We then repeated the process described above 1,000 times and extracted the 5th and 95th percentiles to obtain an estimate of the variability associated with each subject's action spectrum.

Results—

Figure 3B:
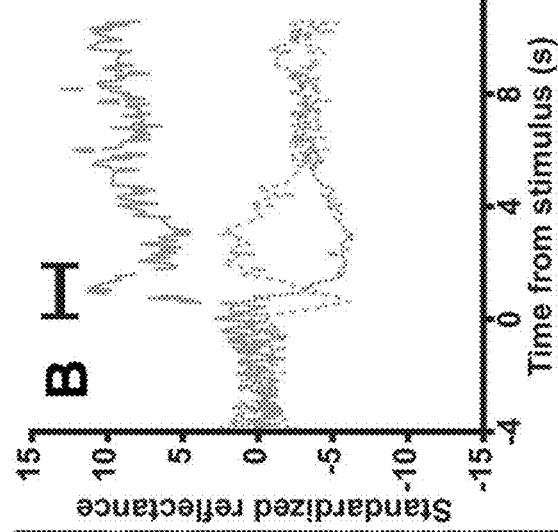
Figure 3A:
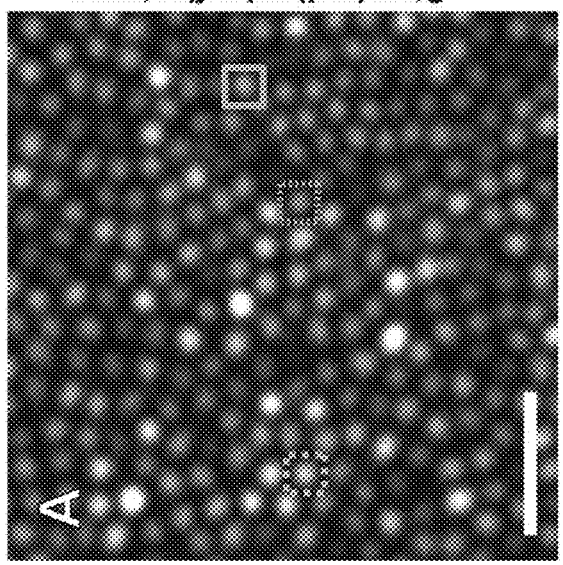

We found that the reflectance of cones changed following visible light stimulation (FIG. 3). After extracting the standardized intrinsic reflectance response of cone photoreceptors (Eq. (2)), we observed that the intrinsic cone reflectance signals were highly heterogeneous: some cones increased their reflectance (FIG. 3B; orange profile), others decreased their reflectance (FIG. 3B; purple profile), and others oscillated (FIG. 3B; cyan profile). Moreover, the form of the response from an individual cone could differ across trials, and not all cones showed a clear response on all trials (FIG. 3C).

Figure 4A:
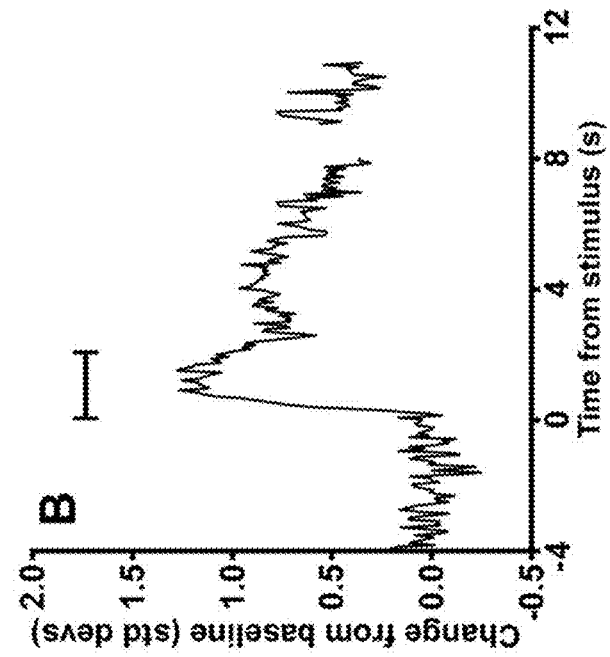
FIG. 4A-4B show the aggregated cone reflectance response, and the cone intrinsic reflectance response measured from the stimulated and control trials using all data from the condition illustrated by FIGS. 3A-3C.
Figure 4B:
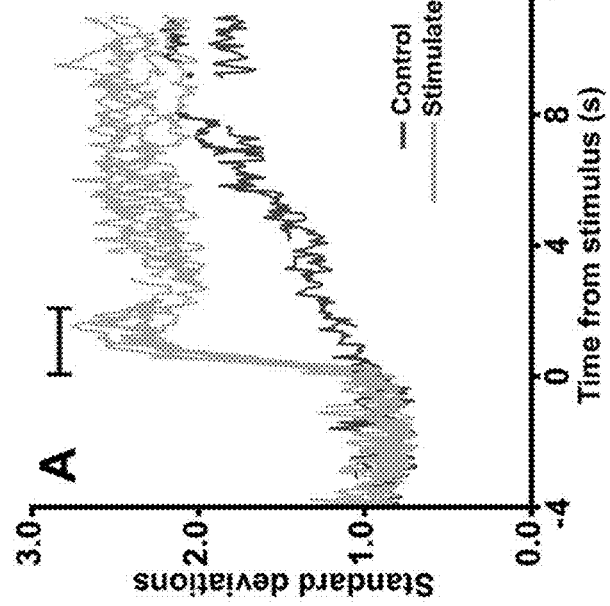
Figures 5A, 5B:
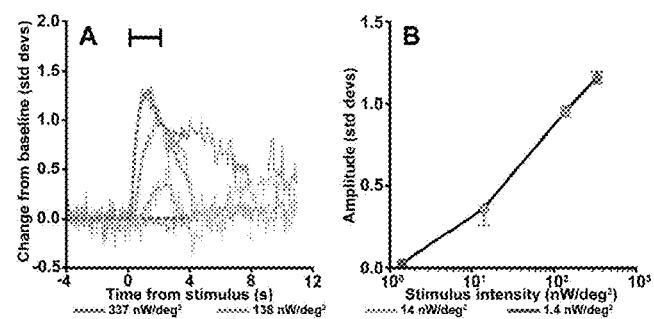
FIGS. 5A and 5B show that the cone reflectance response increases with stimulus irradiance.

Despite this heterogeneity, all cone populations showed a measurable aggregate intrinsic reflectance response (FIG. 4) when it was quantified using our approach. This response was clear and reliable across trials for both stimulated and control conditions, allowing us to pool the results from multiple trials to obtain a final intrinsic reflectance response $\sigma R$ (t) for each condition (FIG. 4B). The intrinsic reflectance response systematically increased with stimulus intensity (FIG. 5A). Extracting the amplitude from the piecewise parametric fit showed an increase in response amplitude with stimulus irradiance (FIG. 5). This relationship held for most wavelengths for all subjects tested (FIG. 10).

Figures 6A, 6B, 6C, 6D, 6E:
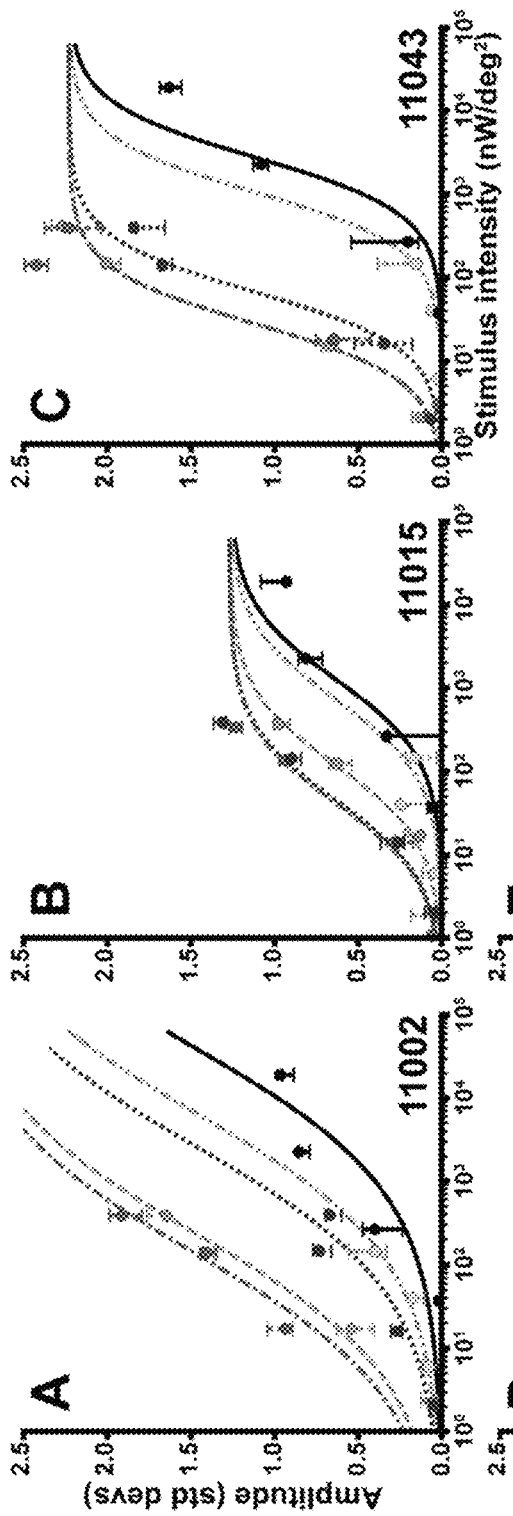
FIGS. 6A-6E are graphs showing the intrinsic reflectance response action spectrum for each subject, i.e.
Figures 7A, 7B:
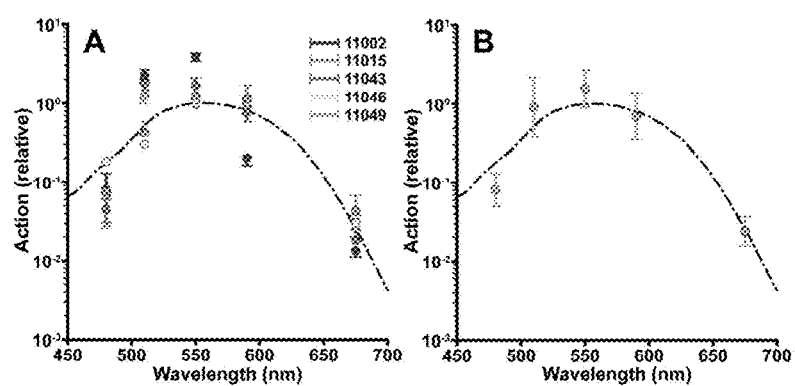
FIGS. 7A-7B show that the wavelength dependence of the reflectance response links it to phototransduction.

In addition to stimulus intensity, the intrinsic reflectance response depended on stimulus wavelength. The dependence is shown in FIG. 6, where we plot each subject's peak amplitude from the fit for all stimulus wavelength/irradiance combinations on a common irradiance axis. From the data, we then found the action spectrum for each subject (determined from the horizontal shift between the sigmoid fit at each stimulus wavelength and the sigmoid fit for the 550 nm stimuli, see above) was well-matched to the human photopic luminosity function (FIG. 7).

Discussion—

We have successfully developed a method that enables extraction of a reliable, quantifiable intrinsic signal from cones imaged using an AOSLO. It is well-known that the number of photoisomerizations in a functioning cone outer segment, as well as the magnitude of the resulting photo-current via phototransduction, increases with stimulus intensity[27]. Thus, if the cone intrinsic reflectance response is related to the physiologic function of the cones, we would expect: 1) its magnitude to be intensity dependent and 2) its action spectrum to match the spectral sensitivity of cone-mediated vision. Indeed, we found that the peak response increased systematically with stimulus intensity for all wavelengths (FIGS. 6 and 10) across all subjects and the action spectrum of the cone intrinsic reflectance response from each subject matched the photopic luminosity function to first order (FIG. 7). These results strongly indicate that the absorption of light by cone photopigment initiates a reflectance response, thereby making the intrinsic reflectance response a direct non-invasive measure of photoreceptor function.

The precise origin of the reflectance changes we measure remains elusive. Previous work has suggested that changes in cone outer segment scattering, refractive index, or structure cause reflectance fluctuations[9]. If the changes in reflectance are due to metabolic changes within each cone, it is uncertain which aspect of phototransduction leads to those changes. The slow time course of the responses suggests a transduction stage downstream from the initial isomerization of photopigment[28-30], or a cellular change that is a consequence of the transduction process, such as swelling or shrinking of the photoreceptor cells[13,28,31,32].

Regardless of the source of the reflectance changes, it is clear that both cone-to-cone and trial-to-trial intrinsic reflectance responses are highly heterogeneous (FIG. 3C). A potential source of this heterogeneity is the stochastic initial state of each cone outer segment. The cone reflectance, or total backscattered light, observed in AOSLO retinal images is thought to arise from a combination of scattered light from each end of the cone outer segment as well as scattering from the discs[33]. The contributions from each of these components may differ across cones at the time of stimulus delivery[34], in which case it is conceivable that a stimulus could evoke a change that either increases or decreases backscattering within a cone, depending on that cone's initial state. Similarly, interference that arises between imaging light reflected from multiple surfaces will depend upon the initial optical path length between the surfaces and the coherence length of the imaging source. If a stimulus leads to a change in the optical path length between the two (or more) reflective surfaces within a cone, then the amount of constructive and destructive interference in that cone can change[9]. Cone-to-cone variations in the initial optical path length would cause the effect of interference (constructive or destructive) to vary across cones in both sign and magnitude.

Grieve et al.[10] reported a slight stimulus-evoked increase in mean cone reflectance, but one that was quite variable. In our preliminary analysis, we did not observe a change in mean reflectance (See, FIG. 9), but a change in reflectance variation. The reason for the difference between our results with respect to mean reflectance and those of Grieve et al.[10] is not immediately clear.

Jonnal et al.[9] also reported that a visible stimulus could increase the variability of cone reflectance measured in the infrared. They used a different set of stimulus parameters and analysis method from ours and did not find an increased response with increased stimulus energy. Specifically, they varied stimulus energy by varying stimulus duration, rather than stimulus irradiance as we did. If we ignore the differences in stimulus duration, and convert our stimulus irradiances to Td·s, the dimmest stimulus used by Jonnal at their stimulating wavelength of 670 nm ($4.2 \times 10^4$ Td·s) is roughly comparable to our highest energy stimulus at a similar wavelength (675 nm, $5.1 \times 10^4$ Td·s). Given that three of our subjects (11002, 11015, 11049) show signs of response saturation at our highest stimulus irradiance, it is possible that Jonnal et al. did not detect a significant response difference across stimulus levels because their responses were approaching saturation. Differences in analysis method or the fact that the coherence length of their imaging source was longer than ours may also contribute to differences in the intensity dependence of the response across the two studies.

The across-wavelength amplitude-irradiance function fits are not perfect (FIG. 6), indicating that the reflectance response satisfies the principle of univariance only in approximation[35]. This is not unexpected, as our measurement combines signals from individual cones of different spectral types in a non-linear manner (both because we use the standard deviation as our aggregation method and because the shape of the individual-cone amplitude-irradiance function is not linear). If it is possible to improve the resolution at which we can measure a reflectance response to the order of a single cone, we predict that each cone's reflectance response will be more closely univariant. Measuring the action spectrum of individual cones may also allow resolution of some of the subject-to-subject differences in the action spectrum calculated from the aggregate signal (FIG. 7A) which in turn may arise from individual variations in L to M cone ratio, lens density and macular pigment density[18,35,36]. Studying individual cones allows us to separate out the contribution of S cones from those of L and M cones.

The agreement between our measured action spectra and the photopic luminosity function differs across subjects. For one subject (11046) it is excellent, while for others there are deviations larger than our estimates of measurement precision. Because the estimates of precision are bootstrapped from a small number of trials, they may themselves be too small. Other factors that might affect the agreement include those discussed in the previous paragraph. We also note that we were limited by our apparatus in the maximum stimulus irradiance available at 480 nm, and that as a result the fit to each subject's 480 nm amplitude irradiance function was not as well-constrained by the data as for other wavelengths.

For this work, calculation of action spectra was based on the assumption that the stimuli were purely monochromatic, while the actual stimuli had finite bandwidth. For the stimulus with the widest bandwidth (480 nm, 30 nm FWHM), we compared the luminance for the actual spectral power distribution (taken to be a Gaussian function of wavelength centered at 480 nm and with a 30 nm FWHM) with that for a purely monochromatic stimulus at 480 nm with the same total irradiance. These differ by less than 0.04 log 10 units, which we regard as too small relative to measurement variability to justify the added complexity of injecting a correction into the analysis.

Figure 8:
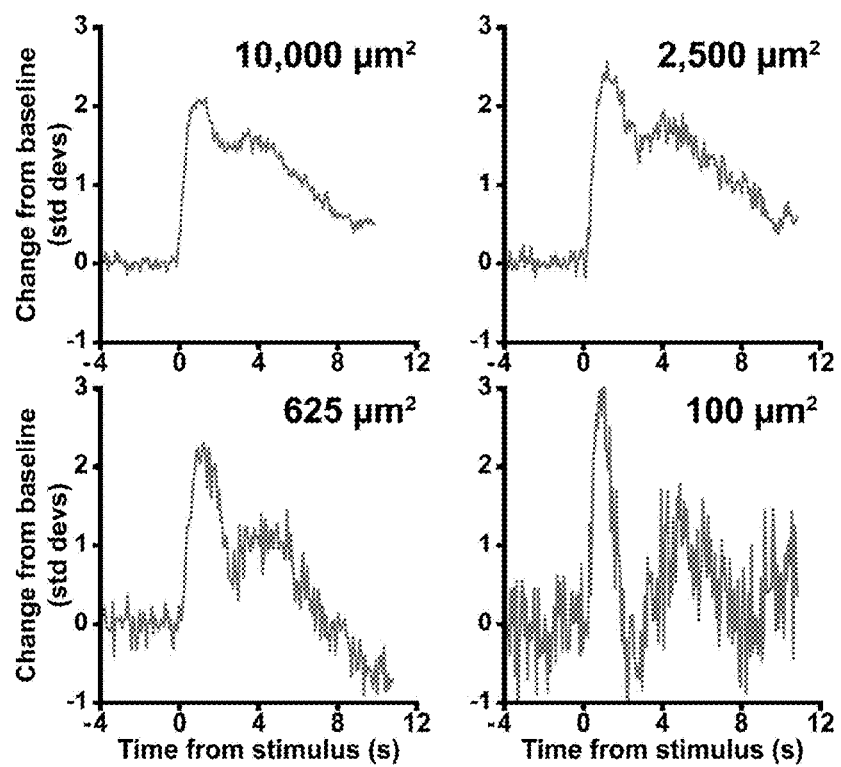
FIG. 8 illustrates the cone photoreceptor intrinsic reflectance response as a function of analysis area. To examine the signal-to-noise characteristics of the response, we selected concentric 10,000, 2,500, 625, and 100 µm² areas for analysis. As region area decreased, the signal to noise ratio of the reflectance response decreased. Despite this, a clear response was observed even from the smallest analysis area. Data was obtained from an irradiance of 337 nW/deg² at 550 nm, from subject 11015. About 5 cones formed the plots. SNR was found to be not quite sufficient with the initial protocol and analysis.

It should be understood that aspects of both the measurement and analysis techniques may be further refined. We focused on one aspect of the reflectance response, amplitude, to assess its action spectrum. We anticipate that extracting other aspects of the reflectance response such as response latency or time-to-peak (FIG. 5A) provides further insight as to the origins of these signals. Other modifications include varying the coherence length of our imaging light to enhance the signal[9], and apparatus modifications to eliminate light leakage from the visible stimulus. However, these data demonstrate that we can reliably extract a stimulus-evoked response in an area as small as 100 μm² (FIG. 8, corresponding to about five cones at ~0.71° from the fovea). In another aspect, the area is reduced further. A 100 μm² analysis window (FIG. 8, bottom right), encompasses area several times smaller than the smallest stimuli used in clinical perimetry (Goldmann I≈830 μm²) and multifocal electroretinography (0.8° diameter hexagons ≈45,000 μm², see also ref 37). Thus, the methods described herein have a functional measurement whose resolution far exceeds that of tools currently available to the clinician.

Crucially, the intrinsic reflectance response is an exciting candidate to provide essential non-invasive functional measurements in diseased eyes. Progressive degeneration of photoreceptors is a major cause of blinding disease[38-40], and experimental therapies (such as gene or small molecule therapy, stem cell transplantation, optogenetic approaches) are being actively developed to prevent and reverse disease progression[41-45]. Each of these therapies operates at the level of individual cells, and evaluation of their effectiveness requires an understanding of both disease etiology and the efficacy of treatment at a similar scale. The intrinsic reflectance response provide a biomarker capable of assessing the restoration of cone function following an experimental intervention.

Example 2: Understanding the Single-Cone Intrinsic Response

To develop and assess methods for measuring an intrinsic reflectance response on a cone-by-cone basis, in the living human retina, the following protocol is developed. The data of Example 1 demonstrates the functional relevance of such a response when signals are aggregated over multiple cones. We optimize our acquisition and analysis parameters to record a maximal reflectance response and adapt our protocols from measuring a response over a population of cells to measuring a response in an individual cell by combining data across multiple trials rather than across multiple cones. The parameters set out in this example were selected for one example; they may be adjusted as described throughout this specification.

We collected data on three subjects following the protocol below. Early data processing (reference frame selection, de-warping, strip registration) on the acquisitions for these subjects was started immediately after data collection, but no substantive analyses were examined. Two hypotheses were examined: (a) Individual cone intrinsic signals are measurable; and (b) individual cone intrinsic signals are sensitive to different stimulus intensities, and their response amplitude is a function of the intensity of the delivered stimulus.

Data Collection—

Three subjects with normal vision are recruited from the five subjects studied in Example 1. Subjects provide informed consent after the nature and possible risks of the study are explained. Each subjects' pupil is dilated and accommodation arrested using one drop each of tropicamide (1%) and phenylephrine (2.5%). Subjects are imaged using an adaptive optics scanning laser ophthalmoscope (AO-SLO). Each image sequence is obtained 0.71° from the subjects' center of fixation at a rate of 16.6 frames per second, using a 795 nm SLD and a 1×1° field of view. The eye studied for each subject matches that previously studied in Example 1 above[46].

This experiment adheres to the following terminological hierarchy (from lowest to highest-level): Acquisition—A single recording as obtained from our laboratory's adaptive optics scanning laser ophthalmoscope. Stimulus/control sequence—The portion of an acquisition corresponding to a stimulus or control condition. Trial—A set of 13 acquisitions (26 stimulus/control sequences), all using a single stimulus condition. Permutation—A randomly ordered set of 3 trials, each with its own stimulus intensity. Session—A single visit by a subject, which will consist of measurements for 5 permutations.

Each acquisition consists of four seconds of prestimulus recording, a two-second stimulus delivered to the entirety of the imaging field, and four seconds of post-stimulus recording, then ten seconds of stimulus-free recording (i.e., 14 seconds of post-stimulus recording in all). This results in 330 images per acquisition. A stimulus or control sequence corresponds to the half of each acquisition with or without a stimulus delivery, respectively, and is obtained by splitting each 330-frame acquisition into a pair of 165-frame image sequences.

Each trial is preceded by two minutes of a dark-adaptation and consists of exactly 13 acquisitions (26 stimulus/control sequences). Previous exploratory analysis has revealed that the first 3 acquisitions contain variable data; thus, the first 3 acquisitions (6 stimulus/control sequences) are discarded from analysis for this study. All acquisitions within a trial use a 550 nm stimulus with a 10 nm full width at half max, and each stimulus condition is defined by three stimulus intensities: 400 nW, 40 nW and 0 nW.

Each permutation consists of 3 randomly ordered trials, each with a different stimulus intensity. A new, random ordering is used for each permutation within a session. If a subject is not able to complete 5 permutations within a single session, the session is aborted and a new complete session rescheduled, to avoid any between-session variability. Similarly, if a post-experimental error in stimulus or recording conditions is discovered, data from that session is discarded and re-collected. If data is discarded for any reason, this is noted. In total, there are 150 acquisitions per subject (10 acquisitions*3 trials*5 permutations) for further analysis.

Data Processing—

Once we acquire the data and split each acquisition in to a stimulus and control sequence, a minimally distorted image is selected from within the stimulus delivery range (image indices 67-99) within each of the sequences (separately for stimulus and control sequences) and used as the reference image for later registration. If there is no minimally distorted image within the stimulus delivery range, or the minimally distorted images are observed to not be from ~0.71° from the fovea, then the sequence is removed from further consideration. Next, we correct the static intra-frame distortion from the sinusoidal motion of the resonant optical scanner by estimating the static spatial distortion from images of a stationary vertical Ronchi ruling and resampling each image over a grid of equally spaced pixels. Each image sequence is "dewarped" in this way, then strip registered to the previously selected (also dewarped) reference image. If fewer than 60% of the images within the stimulus delivery range (image indices 67-99) do not register to the reference image, or if fewer than 60% of the images within a sequence do not register to the reference image, then a new reference frame (within image indices 67-99) is chosen. If fewer than 60% of the images within the stimulus delivery range (image indices 67-99) are unable to register to any reference image or if fewer than 60% of the images within a sequence do not register to any reference image, then the image sequence is removed from further consideration.

Following strip registration, each stimulus or control sequence is placed through a pre-processing pipeline, which consists of the following steps: (1) Residual distortions from eye motion and scanner spatial nonlinearities are removed. The distortions are removed using our variant of Methta's[47] algorithm, and spatial nonlinearities removed by resampling the image based on an exponential fit to a static horizontal Ronchi ruling. (2) The registered sequence is cleaned of any poor data. Specifically, the algorithm determines which regions of the registered sequence are contiguous for the majority of images and removes images that are discontinuous (have registration errors mid-image) or have intensities that are two standard deviations below the sequence mean. (3) The image sequence is then cropped to the new common area. (4) An affine registration is performed on the cleaned, cropped registered sequence to remove any residual image torsion.

All sequences are registered to the sequence with the largest area. An average image is created from all registered sequences, and cone locations in the average image are marked and recorded. Using all image sequences, we exclude cones underlying retinal capillaries by highlighting the vasculature present with a modified version of a previously described algorithm[22]. A binary mask is created from this "motion contrast" image by thresholding values at a single standard deviation greater than the mean. Cones falling within the mask are excluded from analysis. A reflectance signal (reflectance vs time) is created for each cone by first projecting a 3×3 pixel column through the aligned image sequence at each cone location and then averaging the 9 (3×3) pixels in each frame. For each image in the sequence, each cone's reflectance for any given time point is divided by the mean reflectance of all cones at that time point. Each cone signal is standardized with respect to its own prestimulus mean and standard deviation (Example 1). Finally, if a cone does not have a reflectance signal for 90% or more of the stimulus delivery range (image indices 67-99) of any stimulus or control sequence, that cone's signal from that sequence is discarded. We exclude cones from analysis that reach the end of the data processing pipeline with signals retained from fewer than 25 viable stimulus or control sequences for any of the three stimulus intensities, unless this criterion is too stringent and thereby requires reevaluation.

Data Analysis—

To examine the first hypothesis, we summarize the behavior of a single cone for a given stimulus intensity by calculating the standard deviation (defined as the square root of the variance) of its reflectance values across all stimulus and control sequences. The standard deviation of each cone's control sequences is subtracted at each time point from the standard deviation of its stimulus sequences from the same time point. This result at each time point is taken as the cone's intrinsic reflectance response at that time point for a given stimulus intensity. We fit a piecewise smooth function (as in Example 1) to the time course of each cone's reflectance response and determine its peak amplitude.

After the above analyses, each cone has three reflectance response amplitudes corresponding to each of the stimulus intensities (0, 40, and 400 nW). To compare against the previously observed population-based dose-response, we create histograms of the amplitudes from all cones for each stimulus intensity, and calculate descriptive statistics from both of the histograms, such as their mean, median, and what percentage of their values are above 0. We then compare and contrast the descriptive statistics between each of the histograms. These results reveal a population-wide intensity-dependent (or "dose") response similar to Example 1.

We also conduct the following exploratory analyses: (a) We relate each cone's response to its pre-stimulus mean response, to determine if there is a relationship between a cone's pre-stimulus mean and the shape and direction of its reflectance response. (b) We examine whether the mean response of each cone over all of its stimulus and control sequences show a non-zero mean response and explore other ways to extract single cone reflectance signals.

Example 3: Updated Method for Single Cone Analysis

A 2-dimensional reflectance signal (reflectance vs time) for each cone is created by first projecting a 3×3 pixel column through all of the aligned image sequence at each included cone location and then averaging the 9 (3×3) pixels in each frame. One effect of stimulation is to increase the variability of the reflectance within multiple trials of a single cone. The stimulation can also cause an average change in reflectance. To quantify the stimulus-evoked response of a single cell we use multiple techniques or combinations of techniques taking advantage of both properties.

First, to correct for frame-wide changes in image intensity (due to tear film disruption, microsaccades, and changes in AO correction quality), each cone's reflectance for each frame was divided by the mean reflectance of the same frame of all analyzed cones, as in Equation (1):

$$R_{norm}(t)_i = \frac{R_{raw}(t)_i}{\overline{R_{raw}(t)}} \quad (1)$$

where $R_{norm}(t)_i$ is the scaled reflectance of a cone i as a function of time t, and $\overline{R_{raw}(t)}$ is the mean reflectance for the same frame of all analyzed cones.

Second, it is a well-known feature of cone reflectance images that there is cone-to-cone variation in reflectance of unknown origin. To remove this stimulus-independent source of variation from our signals, each cone signal was standardized with respect to its own pre-stimulus mean and standard deviation, as in Equation (2):

$$R(t)_i = \frac{R_{norm}(t)_i - \overline{R_{pre_i}}}{\sigma_{R_{pre_i}}} \quad (2)$$

where $R(t)_i$ is the scaled, standardized reflectance signal from cone i as a function of time t, $\overline{R_{pre_i}}$ is the pre-stimulus reflectance mean for cone i, and $$\sigma_{R_{pre_i}}$$

is the standard deviation of the pre-stimulus reflectance of cone i.

Following this normalization and standardization of each cone reflectance trace, we employ multiple techniques to examine the mean change in cone reflectance and variability of reflectance in multiple traces.

(a) To examine the component of the variability in reflectance observed in the image sequences, we adopted the process described below. Because the intrinsic response is heterogeneous within multiple trials from the same cone, we developed a metric to capture the cone's response over the multiple trials. We calculate the standard deviation across cones' standardized cone reflectance signals at each time point t for all trials.

(b) To examine the average reflectance observed in the image sequences, we adopted the process described below. To eliminate the effect of extrema trials, we calculate the median at each time index of a cone's reflectance profile across all of its stimulus trials.

Using all cones standard deviation (a) or median (b) profiles, we perform a principle component analysis (PCA) on the cone profiles following two seconds after stimulus onset, where the variables of the PCA are the time indexes and the observations are all obtained cone profiles.

The reflectance response for a cone is derived from this first principle component score. Use of the standard deviation (1) PCA score provides similar results to using a combination of PCA scores from both the standard deviation (1) and median (2). The combination of both PCA scores provides a benefit; however, the standard deviation on its own is sufficient.

In addition, we have explored variations on the analysis described in (1) and (2), leading to similar results.

A) We calculate the standard deviation of stimulated trials as described in (1) above, but also calculate the standard deviation of non-stimulated control trials for the same cone. We then subtract the control trials from the stimulated trials.

B) We calculate the median of a stimulated cone's reflectance trials as described in (2) above, but also calculate the median of non-stimulated control trials for the same cone. We then subtract the control trials from the stimulated trials.

We then use PCA for the standard deviations and medians (now control subtracted) as above. The reflectance response for a cone is derived from this first principle component score where the combination of standard deviation and median is superior to standard deviation alone; although standard deviation alone is sufficient. Another embodiment of the analysis involves using one signal employing the control subtraction, while the other does not.

Example 4: Optophysiological Function of Individual Cones

Adaptive optics (AO) observations of the human cone mosaic have shown that visible light stimuli induce changes in infrared reflectivity. In Example 1, we demonstrated that the intrinsic reflectance response for a cone population is dependent on stimulus radiance and wavelength and is related to cone phototransduction. Here we examine whether we can measure an intrinsic reflectance response in individual cones.

Three subjects were imaged using an AO scanning light ophthalmoscope. 1×1° videos were acquired 0.7° from the fovea with a 795 nm imaging source. Each acquisition consisted of recording for 4 s prestimulus, 2 s while delivering a 550 nm stimulus of varying retinal irradiance (0, 50, and 450 nW/deg$^2$), and 14 s post-stimulus. Thirteen acquisitions (the first 3 of which were excluded to allow responses to stabilize) were obtained within a single run. Each run was preceded by 2 minutes of dark adaptation. Five runs were obtained for each stimulus irradiance, with run irradiances randomly interleaved. Every acquisition was split in half; the first and second halves were defined as stimulus and control sequences. All sequences were co-registered. Temporal reflectance signals were extracted from each cone and standardized to their pre-stimulus values. For each stimulus irradiance we calculated the standard deviation (SD) of the standardized reflectances at each time point across all stimulus sequences, subtracted the control sequences' SD, and fit a piecewise-smooth function to the result. We took as each cone's response the signed peak magnitude of that cone's fit.

The average cone response for the 3 subjects was 0.08 (range 0.06-0.1) for 0 nW/deg$^2$, 0.9 (range 0.6-1.2) for 50 nW/deg$^2$, and 1.2 (range 0.8-1.5) for 450 nW/deg$^2$. Larger responses were found in 95% (range 92-97%) of cones at 450 nW/deg$^2$ compared to 0 nW/deg$^2$ and in 92% (range 90-95%) of cones at 50 nW/deg$^2$ compared to 0 nW/deg$^2$.

Our measurements reveal an intrinsic reflectance response in ~95% of individual cones. It is unsurprising that ~5% of cones were unresponsive, as the stimulus wavelength does not substantially activate S-cones. The average individual cone response increases with irradiance, as would be expected for a functional signal. Our technique has the potential to enable simultaneous objective functional assessment of large numbers of individual cones.

Example 5: Cellular-Scale Assessment of Visual Function in Choroideremia

Advanced retinal imaging allows identification of cellular-scale structural abnormalities in retinal disease. Here we use adaptive optics scanning laser ophthalmoscopy (AOSLO) to assess retinal function at high spatial resolution and ask how function varies with structural changes observed in Choroideremia (CHM), an X-linked inherited retinal degeneration.

Structural images of the inner and outer segment mosaics were imaged in twelve CHM patients using a custom AOSLO equipped with both confocal and split-detection imaging modalities. The same instrument was used to make two types of functional measurements.

(1) For AO microperimetry (11 of 12 patients), circular stimuli of 550 nm subtending either 9.6 or 38.3 arcmin$^2$ (~60 or 15 times smaller than Goldman III stimuli) were presented through the AOSLO system. Measurements of transverse chromatic aberration combined with real-time retinal tracking enabled precise targeting of stimuli to pre-identified locations and psychophysical thresholds were measured.

(2) For intrinsic reflectance (7 of 12 patients), infrared confocal images were acquired before, during and following exposure to 550 nm square stimuli subtending 1 deg$^2$. Reflectance responses were extracted for each cone as described in Example 1[46]; these signals are related to phototransduction.

In CHM, both split-detection and confocal structural images show sharp borders between intact central islands of photoreceptors and complete atrophy of the outer retina. AO microperimetry at locations directed across these borders also show a sharp decrease in function, with readily measurable visual thresholds on one side and complete scotoma on the other. Thresholds measured along an outer retinal tubulation showed complete scotoma despite the presence of visible cone inner segments. The average amplitude of the intrinsic reflectance response was reduced by a factor of 6.8 in CHM compared to controls.

CHM patients exhibit sharp functional transitions between intact and degenerated retina. These functional transitions can occur over an area smaller than the Goldman III stimulus. In addition, the intrinsic reflectance response can provide a high throughput biomarker of local cone function in retinal disease. High resolution measures of cone function are important, in particular for assessing whether experimental therapies provide a functional benefit to patients.

Example 6: Determine the Origin of the Intrinsic Reflectance Response

We incorporate dark-field and non-confocal split-detection AOSLO imaging (in comparison with confocal AOSLO) to investigate whether, and to what extent, the intrinsic reflectance response arises from the inner and/or outer segments of the cones and model our results to determine the extent to which interference between the reflectance from the inner segment/outer segment (IS/OS) junction and the reflectance from the cone OS tip can account for the response.

Finally, we correlate the reflectance response with other measures of visual function including retinal sensitivity and multi-focal electroretinogram (mfERG).

To establish reflectance response norms in a population of healthy controls, we investigate how biological variables including retinal eccentricity, age, sex, and race impact the reflectance response. We establish a normative database of the reflectance response across these variables in order to make ready the reflectance response as a biomarker for assessing abnormal cone function. We also compare the reflectance response with other measures of cone function including retinal sensitivity (measured by microperimetry and AO-guided microperimetry) and multi-focal electroretinogram in the same subjects.

Still other experiments are aimed at maximizing the functional signal measured and determining the mechanistic origin of the functional response. Improvements to these methods includes adjustments to both the acquisition of functional images and the analysis of these images. Currently, improvements to the analysis techniques are ongoing, including adjusting how the mean and standard deviation signals are combined for maximum impact.

Example 7: The Reflectance Response of Individual Cones

Stimulus-evoked changes in cone reflectance are heterogeneous both across cones in the mosaic and across trials for individual cones (FIG. 14). Considering that one possible explanation for the origin of the reflectance response is stimulus-evoked changes in interference between light reflected from two or more surfaces within a cone, this heterogeneity is perhaps unsurprising. Indeed we now have data to show that using a coherent light source for imaging results in a higher reflectance response as compared to a partially-coherent light source, as expected given this hypothesis. Our published measurements leveraged the response heterogeneity into a response measure based on reflectance standard deviation, taken across a population of cones for each time point. For single cone responses, we use a similar technique and take advantage of within-cone trial-by-trial response heterogeneity, rather than across-cone heterogeneity.

We measure the intrinsic reflectance response of individual parafoveal cones over a 1° square field in 5 subjects with normal vision. Each subject's pupil is dilated and subjects' parafoveal photoreceptor mosaics are imaged with a NIR coherent light source (785 nm, >95 μm coherence length) using confocal AOSLO. Each data acquisition will consist of four seconds of prestimulus recording, a one-second stimulus delivered to the entirety of the 1° square imaging field, four seconds of post-stimulus recording, and then nine seconds of stimulus-free recording (18 seconds in all). The first nine seconds of recording is the stimulus interval; the last nine seconds is the control interval. These are paired and analyzed as detailed below. Each run of the experiment is preceded by two minutes of a dark-adaptation and consists of 13 acquisitions. Exploratory analysis revealed that the first three acquisitions of a trial are not in steady state; thus, the first three acquisitions are discarded from analysis for this experiment, but stored for possible future analysis. Acquisitions use a 545 nm stimulus with a 10 nm full width at half max (FWHM) and a retinal irradiance of either 900 nW/deg2 or 0 nW/deg2. Stimulating at 545 nm produces close to equal excitation of middle (M) and long-wavelengh sensitive (L) cones (~95% of all cones), and little excitation of short-wavelength-sensitive (S) cones (~5% of cones). The 0 nW/deg2 (i.e. no stimulus) acquisitions will serve to determine the noise floor for the measurement procedure. We acquire five runs for each stimulus irradiance, resulting in 50 retained acquisitions per stimulus irradiance.

For analysis of the reflectance response, each acquisition's series of images are dewarped and co-aligned to each other. Cones are identified in the image sequences and cones underlying retinal capillaries will be excluded from analysis. A reflectance signal (reflectance vs time) is created for each cone by first projecting a 3×3 pixel column through the aligned image sequence at each cone location and then averaging the 9 (3×3) pixels in each frame. For each image in the sequence, each cone's reflectance for any given time point is divided by the mean reflectance of all cones at that time point. Each cone signal is then standardized with respect to its own prestimulus mean and standard deviation, as previously described. An acquisition for a cone is excluded if the cone does not receive at least 90% of a stimulus (due to eye motion or blinks). Cones with fewer than 20 retained acquisitions (out of 50) are excluded from further analysis. We summarize the behavior of a single cone by calculating the standard deviation of its reflectance values at each time point across all stimulus intervals, and separately across all control intervals. The mean standard deviation obtained from all control intervals is subtracted at each time point from the standard deviation obtained from each cone's stimulus intervals to obtain each cone's response (FIG. 15C, black trace). To reject noise fluctuations in the response, we fit the result with a smooth spline and obtain the peak amplitude of the fit. It is the log of this peak amplitude, after addition of one to stabilize the log transformation, that is plotted in FIGS. 15 and 16.

In another analysis method, we have also analyzed the standard deviation data using a moving root mean square (RMS) analysis. In this implementation, we calculate the moving RMS (using a 5 frame window) of the standard deviation across all stimulus and control sequences. The control (0 nW) mean moving RMS is then subtracted at each time point from the moving RMS of each cone's stimulus sequences; this results at each time point is taken as the cone's intrinsic reflectance response at that time point for a given stimulus. We then determine the 95th percentile of the signal during the stimulus delivery period and use this value as the stimulus amplitude.

For each individual cone, reflectance response amplitudes for simulated and control intervals are compared and 900 nW/deg2 stimulus intervals are compared to 0 nW/deg2 stimulus intervals, where the full experiment and analysis will be repeated without visible light stimulation. Data suggests the stimulus interval response of the vast majority of cones stimulated for 1 s at 900 nW/deg2 exceeds the control interval response (FIG. 15). Similar separation is found when comparing the stimulated response for the same cone to an unstimulated (0 nW/deg2) control condition, (data not shown). We view this initial degree of separation as highly promising for obtaining reliable single-cone reflectance responses. Noteworthy is that ~5% of the cones in the human retina are S cones which would not be expected to respond to the 545 nm stimulus, and that the majority of cones we have preliminarily identified as S cones using separate AO densitometry measurements exhibit stimulated reflectance responses that are similar to control responses. We know that the population reflectance response varies with irradiance, duration, and wavelength. Further, we have data (not shown) that indicates that the average individual cone reflectance response increases with stimulus irradiance.

Example 8: Response Repeatability

To test within session repeatability, we randomly divided the 50 acquired trials in half, calculated the reflectance response for each half independently, and compared the reflectance responses of individual cones for the split data set. To test across session repeatability we repeated the experimental acquisitions, using the same imaging and stimulus parameters at the same parafoveal retinal location in the same subject at the same time of day, with more than one week separation. This separation is long enough that the starting reflectance of cones is uncorrelated across time points. Data show that the reflectance response of individual cones is correlated both within and across sessions (FIG. 16). Further, we found that S cones generally did not show a reflectance response to 545 nm stimuli, as expected. We compared intersession response measurements with AO densitometry to validate the extent to which low responding cones are identified as S cones. Preliminary data show that AO densitometry is working in our lab (FIG. 16A); improved identification of S cones will be obtained by taking more data per subject.

Example 9: Effect of Imaging Source Coherence Length

Figure 17:
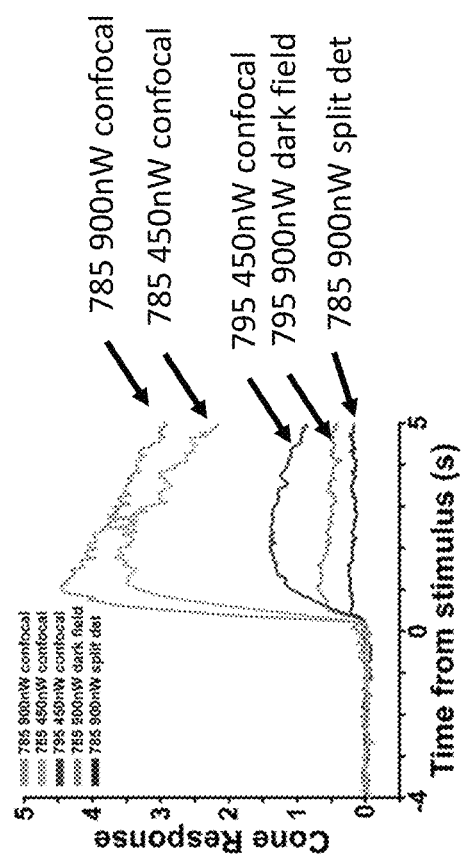
FIG. 17 shows the across-cone population reflectance response increases with coherence length (795 450 nW confocal compared to 785 450 nW confocal lines), increases with stimulus irradiance (785 900 nW confocal compared to 785 450 nW confocal lines), and is measurable and outside of the noise floor (see response at times before stimulus) for confocal, dark-field and split-detection imaging modalities (785 900 nW confocal, 785 900 nW dark field, and 785 900 nW split det lines).

We have measured the reflectance response while varying coherence length of the imaging source. Coherence length is a function of both the wavelength and bandwidth of the source; our data has been acquired using either a 785 nm laser diode or a 795 nm super-luminescent diode with coherence lengths of >95 and 13.6 μm, respectively, assuming a cone outer segment refractive index of 1.43. We have data (FIG. 17; 785 versus 795 nm lines at 450 nW/deg2) to show that imaging with the longer coherence length source results in a stronger reflectance response, as expected.

Example 10: The Multiply-Scattered Reflectance Response

We are testing the hypothesis that the intrinsic reflectance response has a component arising from the cone IS/OS junction using non-confocal split-detection and dark-field AOSLO imaging. Non-confocal split-detection images are thought to show cone ISs by detecting multiply-scattered light in two opposing directions and subtracting one from the other. Dark-field images are the sum of these same two multiply-scattered signals. We are examining the extent to which cones exhibit split-detection and dark-field intrinsic reflectance responses, and the extent to which the split-detection and dark-field responses are affected by imaging coherence length and are correlated with confocal responses. Based on preliminary data from one subject at 1.5° temporal retina (FIG. 17), we have shown that dark-field and split-detection modalities exhibit reflectance responses above the noise floor, but these responses are smaller than the confocal response of the same cells.

Each and every patent, patent application, and publication, including websites cited throughout specification, is incorporated herein by reference. While the invention has been described with reference to particular embodiments, it is appreciated that modifications can be made without departing from the spirit of the invention. Such modifications are intended to fall within the scope of the appended claims.

REFERENCES

1. J. Liang, et al, "Supernormal vision and high-resolution retinal imaging through adaptive optics," J. Opt. Soc. Am. A 14(11), 2884-2892 (1997).
2. A. Roorda, et al, "Adaptive optics scanning laser ophthalmoscopy," Opt. Express 10(9), 405-412 (2002).
3. A. Dubra and Y. Sulai, "Reflective afocal broadband adaptive optics scanning ophthalmoscope," Biomed. Opt. Express 2(6), 1757-1768 (2011).
4. W. Drexler, "Ultrahigh-resolution optical coherence tomography," J. Biomed. Opt. 9(1), 47-74 (2004).
5. W. Makous, et al, "Retinal microscotomas revealed with adaptive-optics microflashes," Invest. Ophthalmol. Vis. Sci. 47(9), 4160-4167 (2006).
6. K. E. Talcott, et al, "Longitudinal study of cone photoreceptors during retinal degeneration and in response to ciliary neurotrophic factor treatment," Invest. Ophthalmol. Vis. Sci. 52(5), 2219-2226 (2011).
7. A. V. Cideciyan, et al, "Human cone visual pigment deletions spare sufficient photoreceptors to warrant gene therapy," Hum. Gene Ther. 24(12), 993-1006 (2013).
8. K. Ratnam, et al., "Relationship between foveal cone structure and clinical measures of visual function in patients with inherited retinal degenerations," Invest. Ophthalmol. Vis. Sci. 54(8), 5836-5847 (2013).
9. R. S. Jonnal, et al, "In vivo functional imaging of human cone photoreceptors," Opt. Express 14, 16141-16160 (2007).
10. K. Grieve and A. Roorda, "Intrinsic signals from human cone photoreceptors," Invest. Ophthalmol. Vis. Sci. 49(2), 713-719 (2008).
11. J. Rha, et al, "Variable optical activation of human cone photoreceptors visualized using a short coherence light source," Opt. Lett. 34(24), 3782-3784 (2009).
12. D. Hillmann, et al, "In vivo optical imaging of physiological responses to photostimulation in human photoreceptors," Proc. Natl. Acad. Sci. U.S.A. 113(46), 13138-13143 (2016).
13. P. Zhang, et al., "In vivo optophysiology reveals that G-protein activation triggers osmotic swelling and increased light scattering of rod photoreceptors," Proc. Natl. Acad. Sci. U.S.A. 114(14), E2937-E2946 (2017).
14. J. I. W. Morgan, et al, "Light-induced retinal changes observed with high-resolution autofluorescence imaging of the retinal pigment epithelium," Invest. Ophthalmol. Vis. Sci. 49(8), 3715-3729 (2008).
15. P. K. Ahnelt, et al., "Identification of a subtype of cone photoreceptor, likely to be blue sensitive, in the human retina," J. Comp. Neurol. 255(1), 18-34 (1987).
16. A. Roorda and D. R. Williams, "The arrangement of the three cone classes in the living human eye," Nature 397(6719), 520-522 (1999).
17. J. Carroll, J et al, "Estimates of L:M cone ratio from ERG flicker photometry and genetics," J. Vis. 2(8), 531-542 (2002).
18. H. Hofer, et al, "Organization of the human trichromatic cone mosaic," J. Neurosci. 25(42), 9669-9679 (2005).
19. L. T. Sharpe, et al, "A luminous efficiency function, V*($\lambda$), for daylight adaptation," J. Vis. 5(11), 948-968 (2005).
20. R. S. Jonnal, et al, "Imaging outer segment renewal in living human cone photoreceptors," Opt. Express 18(5), 5257-5270 (2010).
21. S. L. Polyak, The Retina (The University of Chicago Press, 1941).
22. J. Tam, et al, "Noninvasive visualization and analysis of parafoveal capillaries in humans," Invest. Ophthalmol. Vis. Sci. 51(3), 1691-1698 (2010).
23. A. Dubra and Z. Harvey, "Registration of 2D images from fast scanning ophthalmic instruments," in Biomedical Image Registration, B. Fischer, B. Dawant, and C. Lorenz, eds. (Springer-Verlag, 2010), pp. 60-71.
24. R. Garrioch, et al, "Repeatability of in vivo parafoveal cone density and spacing measurements," Optom. Vis. Sci. 89(5), 632-643 (2012).
25. A. Pallikaris, et al, "The reflectance of single cones in the living human eye," Invest. Ophthalmol. Vis. Sci. 44(10), 4580-4592 (2003).
26. R. F. Cooper, et al, "Spatial and temporal variation of rod J. L. Schnapf, B. J. Nunn, M. Meister, and D. A. Baylor, "Visual transduction in cones of the monkey *Macaca fascicularis*," J. Physiol. 427, 681-713 (1990).
28. K. P. Hofmann, et al, "Measurements on fast light-induced light-scattering and -absorption changes in outer segments of vertebrate light sensitive rod cells," Biophys. Struct. Mech. 2(1), 61-77 (1976).
29. H. Kuhn, et al, "Interactions between photoexcited rhodopsin and GTP binding protein: kinetic and stoichiometric analyses from light-scattering changes," Proc. Natl. Acad. Sci. U.S.A. 78(11), 6873-6877 (1981).
30. V. Y. Arshaysky, et al., "G proteins and phototransduction," Annu. Rev. Physiol. 64, 153-187 (2002).
31. K. P. Hofmann, et al, "Light-induced axial and radial shrinkage effects and changes of the refractive index in isolated bovine rod outer segments and disc vesicles: physical analysis of near infrared scattering changes," Biophys. Struct. Mech. 8(1-2), 67-93 (1981).
32. Y. B. Zhao and X. C. Yao, "Intrinsic optical imaging of stimulus-modulated physiological responses in amphibian retina," Opt. Lett. 33(4), 342-344 (2008)
32. Y. B. Zhao and X. C. Yao, "Intrinsic optical imaging of stimulus-modulated physiological responses in amphibian retina," Opt. Lett. 33(4), 342-344 (2008).
33. J. van de Kraats, et al, "The pathways of light measured in fundus reflectometry," Vision Res. 36(15), 2229-2247 (1996).
34. M. Pircher, et al, "Temporal changes of human cone photoreceptors observed in vivo with SLO/OCT," Biomed. Opt. Express 2(1), 100-112 (2010).
35. D. H. Brainard and A. Stockman, Colorimetry (McGraw-Hill, 2010).

36. G. Wyszecki and W. S. Stiles, Color Science: Concepts and Methods, Quantitative Data and Formulae (John Wiley & Sons, Inc., 1982).
37. C. M. Poloschek and E. E. Sutter, "The fine structure of multifocal ERG topographies," J. Vis. 2(8), 577-587 (2002).
38. J. L. Duncan, et al, "High-resolution imaging with adaptive optics in patients with inherited retinal degeneration," Invest. Ophthalmol. Vis. Sci. 48(7), 3283-3291 (2007).
39. S. Zayit-Soudry, et al, "Cone structure imaged with adaptive optics scanning laser ophthalmoscopy in eyes with nonneovascular age-related macular degeneration," Invest. Ophthalmol. Vis. Sci. 54(12), 7498-7509 (2013).
40. J. I. Morgan, et al, "High resolution adaptive optics retinal imaging of cellular structure in Choroideremia," Invest. Ophthalmol. Vis. Sci. 55(10), 6381-6397 (2014).
41. A. M. Maguire, et al., "Age-dependent effects of RPE65 gene therapy for Leber's congenital amaurosis: A phase 1 dose-escalation trial," Lancet 374(9701), 1597-1605 (2009).
42. K. Zhang, et al, "Ciliary neurotrophic factor delivered by encapsulated cell intraocular implants for treatment of geographic atrophy in age-related macular degeneration," Proc. Natl. Acad. Sci. U.S.A. 108(15), 6241-6245 (2011).
43. D. Dalkara and J. A. Sahel, "Gene therapy for inherited retinal degenerations," C. R. Biol. 337(3), 185-192 (2014).
44. O. Yizhar, et al, "Optogenetics in neural systems," Neuron 71(1), 9-34 (2011).
45. J. C. Giacalone, et al, "Concise review: patient-specific stem cells to interrogate inherited eye disease," Stem Cells Transl. Med. 5(2), 132-140 (2016).
46. C. Cooper et al, October 2017, "Non-invasive assessment of human cone photoreceptor function," Biomed. Optics Express, 8(11): 5098-5112
47. Bedggood, P. and Metha, A., April 2017, De-warping of images and improved eye tracking for the scanning laser ophthalmoscope, PLoS ONE, 12(4): e0174617)

The invention claimed is:

1. A method for non-invasive assessment of photoreceptor function in a mammalian subject comprising:
   exposing a subject's eye to a visible light stimulus, wherein absorption of visible light by a photoreceptor's photopigment initiates an intrinsic reflectance response from the photoreceptor;
   capturing multiple images of the photoreceptor's intrinsic reflectance response to the stimulus over a time period;
   generating a reflectance profile for the photoreceptor from the images;
   calculating the intrinsic reflectance response of the photoreceptor; and
   identifying a pattern of variations in the intrinsic reflectance response indicative of an ocular condition, disease, disorder or a response to treatment for said ocular condition, disease or disorder.

2. The method according to claim 1, further comprising generating a scaled reflectance profile by_quantifying the stimulus-evoked variability in the images by correcting for changes in image intensity in the image frame using Equation (1)

$$R_{norm}(t)_i = \frac{R_{raw}(t)_i}{R_{raw}(t)}$$

where $R_{norm}(t)_i$ is the scaled reflectance of a cone i as a function of time t, and $R_{raw}(t)$ is the mean reflectance for the same frame of all analyzed cones.

3. The method according to claim 1, further comprising classifying photoreceptors according to the condition of the subject.

4. The method according to claim 1, further comprising generating a scaled reflectance profile for the photoreceptor from the reflectance profile; and
   generating a scaled, standardized reflectance profile for the photoreceptor from the scaled reflectance profile.

5. The method according to claim 4, wherein the scaled, standardized reference profile is generated by removing stimulus-independent sources of variation from the images by using Equation (2)

$$R(t)_i = \frac{R_{norm}(t)_i - \overline{R_{pre_i}}}{\sigma_{R_{pre_i}}}$$

where $R(t)_I$ is the scaled, standardized reflectance signal from cone I as a function of time t, $R_{pre\ L}$ is the pre-stimulus reflectance mean for cone i, and $\sigma_{R\ pre\ i}$ is the standard deviation of the pre-stimulus reflectance of cone i.

6. A method for non-invasive assessment of the function of a single photoreceptor in a mammalian subject comprising:
   exposing a subject's eye to a visible light stimulus, wherein absorption of visible light by photoreceptor photopigment initiates an intrinsic reflectance response;
   capturing multiple images of a single photoreceptor's intrinsic reflectance response to the stimulus;
   repeating the exposing and capturing trials for the single photoreceptor using different light stimulus wavelengths, intensities, and intervals to obtain multiple reflectance traces of the single photoreceptor;
   normalizing and standardizing each photoreceptor reflectance trace; and
   obtaining the mean change in photoreceptor reflectance and variability of reflectance in multiple traces; and
   identifying a pattern of variability in the intrinsic reflectance response indicative of an ocular condition, disease, disorder or a response to treatment for said ocular condition, disease or disorder.

7. The method according to claim 6, further comprising one or more of:
   capturing an image of the intrinsic reflectance of the photoreceptor before the stimulus;
   capturing an image of the photoreceptor during the stimulus; and
   capturing an image of the photoreceptor after the stimulus.

8. The method according to claim 6, wherein the stimulus is varied in one or more of wavelength, intensity and duration.

9. The method according to claim 6, wherein the stimulus and image capturing occur at repeated regular or irregular intervals.

10. The method according to claim 6, wherein a variation is one or more of an increase in brightness of reflectance, a decrease in brightness of reflectance, or an oscillation in brightness of said reflectance.

11. The method according to claim 6, further comprising exposing the subject's eye to varying wavelengths of irradiance.

12. The method according to claim 1, wherein the photoreceptor is a population of photoreceptors within a defined analysis area.

13. The method according to claim 12, further comprising capturing a photoreceptor population response by pooling intrinsic reflectance responses with an image frame of a selected dimension for each condition.

14. The method according to claim 6, wherein the photoreceptor is a single rod or cone photoreceptor.

15. The method according to claim 6, wherein the images comprise a photoretinograph, data on a graph, or numerical data.

16. The method according to claim 6, wherein said images are obtained using an ophthalmoscope enhanced with adaptive optics.

17. The method according to claim 16, wherein said ophthalmoscope comprises a light source for applying the visible light stimulus and is associated with a computer program directing the wavelength, intensity, repetition and timing of the visible light stimulus application.

18. The method according to claim 6, wherein said images are captured by a fundus camera.

19. The method according to claim 6, which is computer-implemented.

20. The method according to claim 6, further comprising obtaining photoreceptor standardized photoreceptor reflectance signals at each time point t for all stimulus trials and calculating: the standard deviations thereof to obtain a photoreceptor standard deviation profile, the median at each time index of a photoreceptor's reflectance profile across all of its stimulus trials to obtain a photoreceptor median profile, or both.

21. The method according to claim 6, further comprising performing a principal component analysis (PCA) on the photoreceptor profile, wherein the reflectance response for the single photoreceptor is derived from the PCA score.

22. The method according to claim 21, which employs one or a combination of a photoreceptor standard deviation profile, a photoreceptor median profile, a photoreceptor standard deviation profile from which a control value has been subtracted, or a photoreceptor median profile from which a control value has been subtracted.

23. An apparatus comprising an adaptive optics-enhanced ophthalmoscope, a light source for applying visible light stimulus to initiate an intrinsic reflectance response in a subject's eye; and a non-transitory computer readable storage medium directing the wavelength, intensity, and timing of the stimulus application and the timing of imaging the variability in the photoreceptor's intrinsic reflectance in response to the stimulus for a non-invasive assessment of photoreceptor function.

* * * * *

UNITED STATES PATENT AND TRADEMARK OFFICE
CERTIFICATE OF CORRECTION

| | |
|---|---|
| PATENT NO. | : 11,607,125 B2 |
| APPLICATION NO. | : 16/389942 |
| DATED | : March 21, 2023 |
| INVENTOR(S) | : Jessica I. W. Morgan et al. |

It is certified that error appears in the above-identified patent and that said Letters Patent is hereby corrected as shown below:

In the Claims

Column 33, Line 57, Claim 2 is amended as follows:
--generating a scaled reflectance profile by quantifying the stimulus-evoked variability--

Column 36, Line 1, Claim 20 is amended as follows:
--reflectance signals at each time point $t$ for all stimulus trials--

Signed and Sealed this
Twenty-sixth Day of September, 2023

Katherine Kelly Vidal
*Director of the United States Patent and Trademark Office*